United States Patent
Bellini et al.

(10) Patent No.: US 11,382,977 B2
(45) Date of Patent: Jul. 12, 2022

(54) BIOPHOTONIC COMPOSITIONS FOR TREATING SKIN AND SOFT TISSUE WOUNDS HAVING EITHER OR BOTH NON-RESISTANT AND RESISTANT INFECTIONS

(71) Applicant: VETOQUINOL S.A., Lure (FR)

(72) Inventors: Francesco Bellini, Calgary (CA); Alberto Salvaggio, Matelica (IT); Angela Palumbo Piccionello, Matelica (IT); Andrea Spaterna, Matelica (IT); Nikolaos Loupis, Athens (GR); Lise Hebert, Montreal (CA); David Ohayon, Dollard-des-Ormeaux (CA); Remigio Piergallini, San Benedetto del Tronto (IT); Cecilia Vullo, Castelraimondo (IT)

(73) Assignee: VETOQUINOL S.A., Lure (FR)

( * ) Notice: Subject to any disclaimer, the term of this patent is extended or adjusted under 35 U.S.C. 154(b) by 0 days.

(21) Appl. No.: 16/068,714

(22) PCT Filed: Jan. 11, 2017

(86) PCT No.: PCT/CA2017/050036
§ 371 (c)(1),
(2) Date: Jul. 9, 2018

(87) PCT Pub. No.: WO2017/120674
PCT Pub. Date: Jul. 20, 2017

(65) Prior Publication Data
US 2019/0022219 A1    Jan. 24, 2019

Related U.S. Application Data

(60) Provisional application No. 62/277,286, filed on Jan. 11, 2016.

(51) Int. Cl.

| | | |
|---|---|---|
| *A61K 41/00* | (2020.01) | |
| *A61K 31/17* | (2006.01) | |
| *A61K 31/352* | (2006.01) | |
| *A61P 31/04* | (2006.01) | |
| *A61P 1/02* | (2006.01) | |
| *A61P 17/02* | (2006.01) | |
| *A61K 31/327* | (2006.01) | |
| *A61K 31/4166* | (2006.01) | |
| *A61K 31/7008* | (2006.01) | |
| *A61K 31/728* | (2006.01) | |
| *A61K 33/40* | (2006.01) | |
| *A61N 5/06* | (2006.01) | |

(52) U.S. Cl.
CPC .......... *A61K 41/0057* (2013.01); *A61K 31/17* (2013.01); *A61K 31/327* (2013.01); *A61K 31/352* (2013.01); *A61K 31/4166* (2013.01); *A61K 31/7008* (2013.01); *A61K 31/728* (2013.01); *A61K 33/40* (2013.01); *A61N 5/062* (2013.01); *A61P 1/02* (2018.01); *A61P 17/02* (2018.01); *A61P 31/04* (2018.01); *A61N 2005/0651* (2013.01); *A61N 2005/0662* (2013.01); *A61N 2005/0663* (2013.01)

(58) Field of Classification Search
CPC ................ A61K 41/0057; A61K 31/17; A61K 31/327; A61K 31/352; A61K 31/4166; A61K 31/7008; A61K 31/728; A61K 33/40; A61P 1/02; A61P 17/02; A61P 31/04; A61N 5/062; A61N 2005/0651; A61N 2005/0662; A61N 2005/0663
See application file for complete search history.

(56) References Cited

U.S. PATENT DOCUMENTS

| | | |
|---|---|---|
| 3,141,321 A | 7/1964 | Rinaldi |
| 4,402,959 A | 9/1983 | Dybas et al. |
| 4,430,381 A | 2/1984 | Harvey et al. |
| 4,533,435 A | 8/1985 | Intili |
| 4,625,026 A | 11/1986 | Kim |
| 4,736,467 A | 4/1988 | Schwarze et al. |
| 4,855,139 A | 8/1989 | Srinivasan |
| 5,069,907 A | 12/1991 | Mixon et al. |
| 5,091,102 A | 2/1992 | Sheridan |
| 5,529,769 A | 6/1996 | Cho et al. |
| 5,639,464 A | 6/1997 | Terry et al. |
| 5,853,883 A | 12/1998 | Nohr et al. |
| 5,854,147 A | 12/1998 | Nohr et al. |

(Continued)

FOREIGN PATENT DOCUMENTS

| | | |
|---|---|---|
| WO | 2010051636 A1 | 5/2010 |
| WO | 2011006263 A1 | 1/2011 |

(Continued)

OTHER PUBLICATIONS

Garcez et al. Antimicrobial mechanisms behind photodynamic effect in the presence of hydrogen peroxide. Photochem Photobiol Sci. Apr. 30, 2011; 10(4): 483-490. (Year: 2011).*

(Continued)

*Primary Examiner* — Robert A Wax
*Assistant Examiner* — Olga V. Tcherkasskaya
(74) *Attorney, Agent, or Firm* — BCF LLP

(57) ABSTRACT

The present document describes methods and uses of biophotonic compositions which comprise at least one oxidant and at least one chromophore capable of activating the oxidant, in association with a pharmacologically acceptable carrier for use in the treatment of skin and soft tissue wounds that have either or both non-resistant and resistant infections.

13 Claims, 38 Drawing Sheets

(56) References Cited

U.S. PATENT DOCUMENTS

| | | | |
|---|---|---|---|
| 5,894,042 | A | 4/1999 | Ferralli |
| 5,919,554 | A | 7/1999 | Watterson, III et al. |
| 6,203,805 | B1 | 3/2001 | Collins et al. |
| 7,598,291 | B2 | 10/2009 | Nimni et al. |
| 7,722,904 | B2 | 5/2010 | Schneider et al. |
| 2004/0009227 | A1 | 1/2004 | Yao |
| 2006/0247313 | A1 | 11/2006 | Murakami et al. |
| 2008/0108681 | A1 | 5/2008 | Scimeca et al. |
| 2009/0069217 | A1 | 3/2009 | Kato et al. |
| 2009/0220450 | A1 | 9/2009 | Green et al. |
| 2009/0325885 | A1 | 12/2009 | Miyata et al. |
| 2011/0081530 | A1 | 4/2011 | Robinson et al. |
| 2011/0086060 | A1 | 4/2011 | Bidamant et al. |
| 2011/0130459 | A1 | 6/2011 | Spencer |

FOREIGN PATENT DOCUMENTS

| | | |
|---|---|---|
| WO | 2013155620 A1 | 10/2013 |
| WO | 2014040176 A1 | 3/2014 |
| WO | 2015000058 A1 | 1/2015 |

OTHER PUBLICATIONS

Worthington et al. Combination Approaches to Combat Multi-Drug Resistant Bacteria. Trends Biotechnol. Mar. 2013; 31(3):177-184. (Year: 2013).*

De Oliveira et al., "Photodynamic therapy in combating the causative microorganisms from endodontic infections", Eur. J. Dent., 2014 8(3), 424-430.

Gonzales et al., "Photodynamic inactivation of microorganisms as an innovative approach to kill mucocutaneous and skin microorganisms", Giornale Italiano Di Dermatologia e Venereologia, 2010, 145, 477-489.

Maisch et al., "Antibacterial photodynamic therapy in dermatology", Photochemical & Photobiological Sciences, 2004, 3, 907-917.

Lambrechts et al., "Photodynamic therapy for *Straphylococcus aureus* infected burn wound in mice", Photochemical & hotobiological Sciences, 2005, 4(7), 503-509.

Carvalho et al., "Study of photodynamic therapy in the control of isolated microorganisms from infected wounds—A in vitro study", LasersMed. Sci. 2014, 29, 113-120.

Sahu et al., "Modulation of inflammatory response of wounds by antimicrobial photodynamic therapy", Laser Therapy, 2015, 24(3), 201-208.

Sahu et al., "Topical photodynamic therapy with poly-L-lysine-chlorin p6 conjugate improces wound healing by reducing hyperinflammatory response in Pseudomonas aeurginosa-infected wounds of mice", LasersMed. Sci. 2013, 28, 465-471.

Jiang et al., "Toluidine blue-mediated photodynamic therapy of oral wound infected with *Staphylococcus aureus* in rats", Chinese Journal of Conservative Dentistry, 2009, 19(8), 462-465.

Sahu et al., "Topical antimicrobial photodynamic therapy improves angiogenesis in wounds of diabetic mice", Laser Sci. Med., 2015, 30, 1923-1929.

Hashimoto et al.,"Antimicrobial photodynamic therapy on drug-resistant Pseudomonas aeruginosa-induced infection: A in vivo study", Photochemistry and Photobiology, 2012, 88, 590-595.

Vecchio et al., "Antimicrobial photodynamic therapy with RLP068 kills methicillin-resistant *Staphyloccocus aureus* and improves wound healing in a mouse model of infected skin abrasion", Journal of Biophotonics, 2013, 6(9), 733-742.

Lins et al., "Enhancement of Antimicrobial Action of Photodynamic Therapy in the Presence of Hydrogen Peroxide", in "Microbial Pathogens and Strategies for Combating Them: Science, Technology and Education", Edition: Microbiology Book Series 4, Editor: A. Mendez-Vilas, 2013, pp. 367-371.

Caccianiga et al., "Photodynamic therapy (Association diode laser/hydrogen peroxide): Evaluationof bacterial effects on periodintipathic bacteria: An In Vitro study", European Journal of Inflammation, 2012, 10, 101-106.

Awad et al., In Vitro Photodynamic Antimicrobial Activity of Protoporphyrin IX in the Presence of Hydrogen Peroxide against *Staphylococcus aureus* and Pseudomonas aeruginosa, British Microbiology Research Journal, 4(11), 1219-1234.

Durrani et al., "Studies on Drugs Release Kinetics From Carbopol® 934P Tablets", Pharmaceutical Res. Supp. 8: S-135, 1991—abstract only.

Brock et al. "Use of In Vitro and In Vivo Data in the Design, Development, and Quality Control of Sustained-Release Decongestant Dosage Forms", Pharmacotherapy, 1994, vol. 14, pp. 430-437.

Ong et al., "Infections of the External Ear", Annals Academy of Medicine, Singapore, May 2005; vol. 34, No. 4, pp. 330-334.

Silva et al., "Animal models for photodynamic therapy (PDT)", Biosci. Rep. (2015), 35 / art:e00265 / doi 10.1042/BSR20150188.

\* cited by examiner 15 days of treatment

SELECTED 3 ZONES OF TREATMENT:
- left flank
- right flank
- breast district

For each zone were clipped two rectangular areas of different size

ON ALL SMALL AREAS WE APPLIED CHROMOPHORE GEL AND UP 0%

LARGER AREAS:
RIGHT FLANK UP 3%
LEFT FLANK UP 6%
BREAST 12%

LIGHT SOURCE APPLIED WAS BLUE LAMP AT A DISTANCE OF 5cm WITH AN EXPOSITION TIME OF 5 MINUTES

THE DESCRIBED PROTOCOL WAS APPLIED TWO TIMES PER WEEK FOR A TOTAL OF FOUR WEEKS (8 TREATMENTS)

BIOPHOTONIC COMPOSITIONS FOR TREATING SKIN AND SOFT TISSUE WOUNDS HAVING EITHER OR BOTH NON-RESISTANT AND RESISTANT INFECTIONS

RELATED APPLICATIONS

This application claims priority to and benefit from U.S. Provisional Patent Application No. 62/277,286, filed Jan. 11, 2016, the disclosure of which is incorporated herein by reference in its entirety.

TECHNICAL FIELD

This disclosure relates to the field of biophotonic compositions, methods, and uses for treating skin and soft tissue wounds that have either or both non-resistant and resistant infections.

BACKGROUND

Treatment of skin and soft tissue wounds in mammals such as humans, horses, cats, or dogs can be challenging, especially due to infection of the wound, and moreover if the infection becomes a resistant infection. A resistant infection is an infection caused by a microorganism that is resistant to an antimicrobial or anti-infective agent that was originally effective for treatment of infections caused by it. Resistant microorganisms (including bacteria, fungi, viruses and parasites) are able to withstand treatment by antimicrobial or anti-infective agents, such as antibacterial agents (e.g., antibiotics), antifungals, antivirals, and antiprotozoals, so that standard treatments become ineffective and infections persist. As resistant infections fail to respond to standard treatments, they result in prolonged healing, reduced effectiveness of treatment, higher care expenditures, and a greater risk of death.

Effective treatments for the treatment of skin and soft tissue wounds having non-resistant infections or resistant infections or both categories of infections, are needed.

SUMMARY OF THE DISCLOSURE

In some aspects, this disclosure provides new methods of treatment of a skin or soft tissue wound having a non-resistant or a resistant infection or both categories of infections, and makes the management of these infections less frustrating and economically challenging. The compositions, methods, and uses disclosed herein reduce healing time compared to conventional treatments, therefore result in less stress and discomfort to the patient. The compositions, methods, and uses disclosed herein are also easier to use than unconventional treatments, such as platelet-rich plasma therapy and stem cell therapy. Additionally, the compositions, methods, and uses disclosed herein can reduce the microbial load of wounds and are useful in maintaining asepsis during surgeries. The compositions, methods, and uses of the disclosure can be used to treat resistant infections, and even non-resistant infections, of skin and soft tissue wounds without or with reduced use of antibiotics or antimicrobial agents.

In some aspects, this disclosure provides a method of treating a skin or soft tissue wound having a non-resistant or a resistant infection, or both categories of infection, comprising: applying a biophotonic composition to a patient in need thereof, wherein the biophotonic composition comprises at least one oxidant and at least one chromophore capable of activating the oxidant; and exposing said biophotonic composition to actinic light for a time sufficient for said chromophore to cause activation of said oxidant. In certain such aspects, the soft tissue wound comprises an oral disease. In certain such aspects, the wound is a skin wound. In certain aspect, the method promotes the healing of wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline, or a canine. In certain such aspects, the infection is a resistant infection. In certain aspects, the infection is an antibiotic resistant infection.

In some embodiments, said biophotonic composition is exposed to actinic light for a period of less than about 5 minutes, e.g., for a period of from about 1 second to about 5 minutes. In certain such embodiments, said biophotonic composition is exposed to actinic light for a period of less than about 5 minutes per $cm^2$ of an area to be treated, e.g., for a period of about 1 second to about 5 minutes per $cm^2$.

In some embodiments, the source of actinic light is positioned over an area to be treated. In some embodiments, said actinic light is visible light having a wavelength between about 400 nm and about 700 nm.

In some embodiments, the oxidant present in the biophotonic composition is chosen from hydrogen peroxide, carbamide peroxide, and benzoyl peroxide. In other embodiments, the oxidant is chosen from a peroxy acid and an alkali metal percarbonate.

In some embodiments, the biophotonic composition further comprises at least one healing factor chosen from hyaluronic acid, glucosamine, and allantoin.

In some embodiments, the biophotonic composition further comprises at least one gelling agent, such as glucose, modified starch, methyl cellulose, carboxymethyl cellulose, propyl cellulose, hydroxypropyl cellulose, a carbomer, alginic acid, sodium alginate, potassium alginate, ammonium alginate, calcium alginate, agar, carrageenan, locust bean gum, pectin, or gelatin.

In some embodiments, the chromophore of the biophotonic composition is chosen from a xanthene derivative dye, an azo dye, a biological stain, and a carotenoid. In certain such embodiments, said xanthene derivative dye is chosen from a fluorene dye (e.g., a pyronine dye, such as pyronine Y or pyronine B, or a rhodamine dye, such as rhodamine B, rhodamine G, or rhodamine WT), a fluorone dye (e.g., fluorescein, or fluorescein derivatives, such as phloxine B, rose bengal, merbromine, Eosin Y, Eosin B, or Erythrosine B, i.e., Eosin Y), or a rhodole dye. In certain such embodiments, said azo dye is chosen from methyl violet, neutral red, para red, amaranth, carmoisine, allura red AC, tartrazine, orange G, ponceau 4R, methyl red, and murexide-ammonium purpurate. In certain such embodiments, said biological stain is chosen from saffranin O, basic fuchsin, acid fuschin, 3,3' dihexylocarbocyanine iodide, carminic acid, and indocyanine green. In certain such embodiments, said carotenoid is chosen from crocetin, a-crocin (S,S-diapo-S,S-carotenoic acid), zeaxanthine, lycopene, α-carotene, β-carotene, bixin, and fucoxanthine. In certain such embodiments, said carotenoid is present in the composition as a mixture chosen from saffron red powder, annatto extract, and brown algae extract.

In certain embodiments, said biophotonic composition further comprises at least one chelating agent chosen from ethylenediaminetetraacetic acid (EDTA) and ethylene glycol tetraacetic acid (EGTA).

In some aspects, the disclosure provides for use of a biophotonic composition for the manufacture of a medicament for treating a patient afflicted with a skin or soft tissue wound having a non-resistant infection or a resistant infection or both categories of infection, wherein said composition comprises: at least one oxidant, and at least one chromophore capable of activating the oxidant; in association with a pharmacologically acceptable carrier. In certain such aspects, the soft tissue wound comprises an oral disease. In certain such aspects, the wound is a skin wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline or a canine. In certain such aspects, the infection is a resistant infection.

In some aspects, the disclosure provides for use of a biophotonic composition for the treatment of a patient afflicted with a skin or soft tissue wound having a non-resistant or a resistant infection or both categories of infection, wherein said composition comprises: at least one oxidant; and at least one chromophore capable of activating the oxidant; in association with a pharmacologically acceptable carrier. In certain such aspects, the soft tissue wound comprises an oral disease. In certain such aspects, the wound is a skin wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline or a canine. In certain such aspects, the infection is a resistant infection.

Definitions

Before continuing to describe the present disclosure in further detail, it is to be understood that this disclosure is not limited to specific compositions or process steps, as such may vary. It must be noted that, as used in this specification and the appended embodiments, the singular form "a", "an" and "the" include plural referents unless the context clearly dictates otherwise.

It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Biophotonic" means the generation, manipulation, detection and application of photons in a biologically relevant context. In other words, biophotonic compositions exert their physiological effects primarily due to the generation and manipulation of photons. "Biophotonic composition" is a composition as described herein that may be activated by light to produce photons for biologically relevant applications.

"Topical" means as applied to body surfaces, such as the skin, mucous membranes, vagina, oral cavity, internal surgical wound sites, and the like.

Terms "chromophore", "photoactivating agent" and "photoactivator" are used herein interchangeably. A chromophore means a compound, when contacted by light irradiation, is capable of absorbing the light. The chromophore readily undergoes photoexcitation and can then transfer its energy to other molecules or emit it as light.

The term "oxidant" is intended to mean either a compound that readily transfers oxygen atoms to, and thus, oxidizes other compounds, or a substance that gains electrons in a redox chemical reaction.

The term "chelating agent" is intended to mean a compound that binds metal ions, such as iron, cobalt, copper, manganese, and chromium ions, and facilitates their solvation in solution.

The term "healing factor" is intended to mean a compound that promotes or enhances the healing or regenerative process of a tissue.

The term "active oxygen species" is intended to mean chemically-reactive molecules containing oxygen. Examples include, but are not limited to, oxygen ions and peroxides. They can be either inorganic or organic. Active oxygen species are highly reactive due to the presence of unpaired valence shell electrons. They are also referred to as "reactive oxygen", "active oxygen", or "reactive oxygen species".

"Wound" means an injury to any tissue, including, for example but are not limited to, acute, subacute, delayed or difficult to heal wounds, and chronic wounds. Examples of wounds include both open and closed wounds. Wounds include, for example, but are not limited to, burns, incisions, excisions, lesions, lacerations, abrasions, puncture or penetrating wounds, gunshot wounds, surgical wounds, contusions, hematomas, crushing injuries, ulcers (such as for example pressure, venous, pressure or diabetic), wounds caused by periodontitis (inflammation of the periodontium), or other soft tissue disorders.

A "resistant infection" is an infection caused by a microorganism that is resistant to treatment with an antimicrobial or anti-infective agent that was originally effective in treating such an infection. Resistant microorganisms (including bacteria, fungi, viruses and parasites) are able to withstand treatment by antimicrobial or anti-infective agents, such as antibacterial agents (e.g., antibiotics), antifungals, antivirals, and antiprotozoals, so that standard treatments become ineffective and infections persist.

An "anti-infective agent" or an "antimicrobial agent" is an agent that can ameliorate any symptom caused by an infectious agent and may reduce the spread of the infection. Anti-infective or antimicrobial agents include antibiotics and antibacterials, antifungals, antivirals and antiprotozoals.

Features and advantages of the subject matter hereof will become more apparent in light of the following detailed description of selected embodiments, as illustrated in the accompanying figures. As will be realized, the subject matter disclosed is capable of modifications in various respects, all without departing from the scope of the disclosed embodiments. Accordingly, the figures and the description are to be regarded as illustrative in nature, and not as restrictive and the full scope of the subject matter is set forth in the disclosed embodiments.

BRIEF DESCRIPTION OF THE DRAWINGS

Further features and advantages of the present disclosure will become apparent from the following detailed description, taken in combination with the appended drawings, in which:

FIG. 8A shows tissues treated three times with a biophotonic composition comprising 3% by weight urea peroxide. During each treatment, the biophotonic composition was exposed to actinic light for two minutes. The first treatment with the biophotonic composition was performed during surgery. FIG. 8B shows tissues not treated with biophotonic therapy (a control sample).

FIG. 9A shows photographs of the wound before treatment (T0) and after the first and second treatments (T1 and T2). FIG. 9B shows photographs of the wound after the third, fourth, and fifth treatments (T3, T4, and T5). FIG. 9C shows measure of the wound at T0, T1. T2, T3, T4, and T5. FIGS. 9D and 9E illustrate the decrease in the size of the wound during the course of treatment. FIG. 9F shows a comparison in the size of the wound before treatment and after 15 days of treatment. FIG. 9G is a graph with the size of the wound on the y-axis and the days of treatment on the x-axis. The graph illustrates a decrease in the size of the wound during biophotonic therapy treatment.

As shown in FIG. 12A, three zones of treatment where selected, the left flank, the right flank, and the breast. The zones were treated with a biophotonic composition with 0%, 3%, 6%, or 12% urea peroxide (UP) two times per week for a total of 4 weeks. FIG. 12B shows treatment of the zones with blue light.

FIG. 13A illustrates swelling to the left carpal region and two wounds draining purulent material. It also illustrates a fistula located on the palmar surface of the region. FIG. 13B illustrates treatment of the large wound with a biophotonic composition comprising 12% UP and treatment of the small wound with a biophotonic composition comprising 3% UP. FIG. 13C illustrates treatment of the wounds with blue light. FIG. 13D illustrates treatment of the wounds over the course of six weeks.

FIG. 14A shows treatment of the wound with lavage, disinfection, wound suture, drainage, and systemic antibiotic (conventional treatment). FIG. 14B shows dehiscence of the wound after conventional treatment. FIG. 14C shows treatment of the dehisced wound with a 12% UP biophotonic composition and blue light. FIG. 14D shows healing of the wound after one week of treatment and before application of another round of biophotonic therapy. FIG. 14E shows healing of the wound after two applications of biophotonic therapy (two weeks of treatment).

FIG. 19A shows application of the biophotonic composition. FIG. 19B shows photoactivation of the biophotonic composition. FIG. 19C shows scaling and root planing (SRP) of the canine patient.

FIG. 20A shows application of the biophotonic composition. FIG. 20B shows photoactivation of the biophotonic composition.

DETAILED DESCRIPTION

Figure 1:
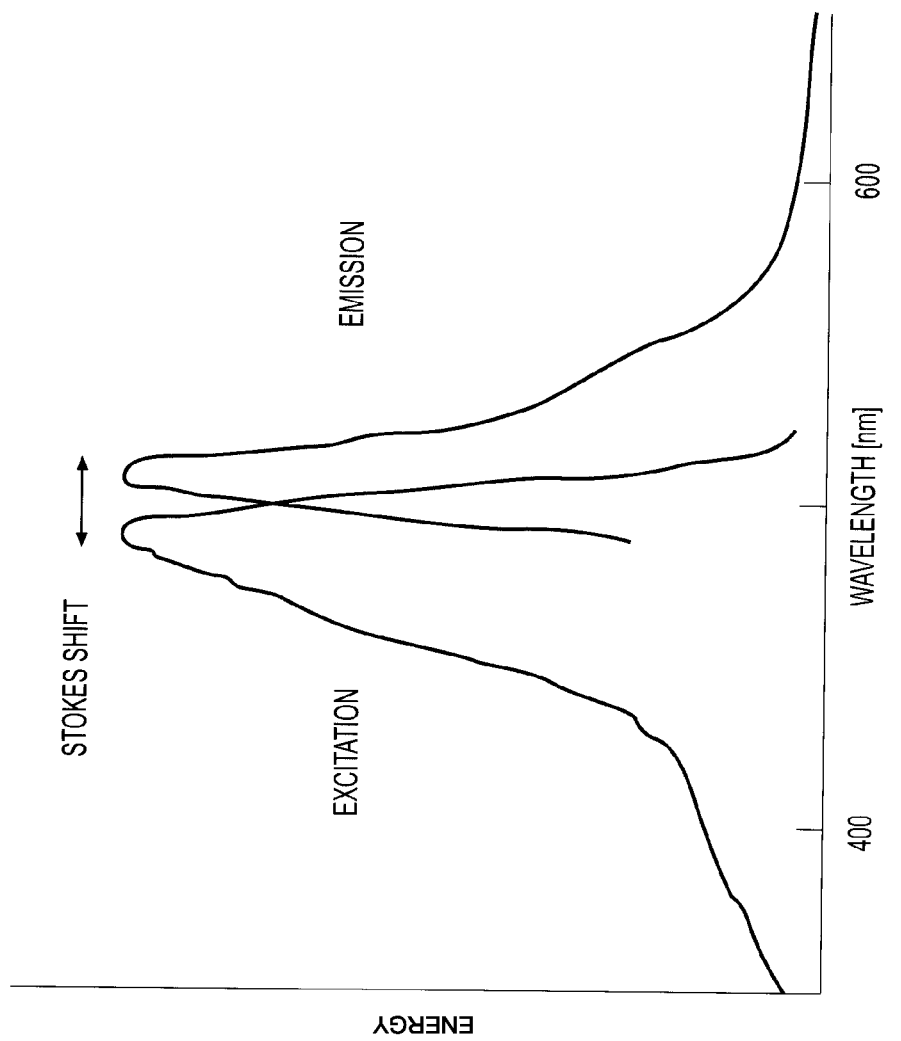
FIG. 1 illustrates the Stokes' shift.

In some aspects, the disclosure provides a method of treating a skin or soft tissue wound having a non-resistant or a resistant infection or both categories of infection, comprising: applying a biophotonic composition to a patient in need thereof, wherein the biophotonic composition comprises at least one oxidant and at least one chromophore capable of activating the oxidant; and exposing said biophotonic composition to actinic light for a time sufficient for said chromophore to cause activation of said oxidant. In certain such aspects, the soft tissue wound comprises an oral disease. In certain such aspects, the wound is a skin wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline or a canine. In certain such aspects, the infection is a resistant infection.

In other aspects, the disclosure provides for use of a biophotonic composition for the manufacture of a medicament for treating a patient afflicted with a skin or soft tissue wound having a non-resistant or a resistant infection or both categories of infection, wherein said composition comprises: at least one oxidant, and at least one chromophore capable of activating the oxidant; in association with a pharmacologically acceptable carrier. In certain such aspects, the soft tissue wound comprises an oral disease. In certain such aspects, the wound is a skin wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline or a canine. In certain such aspects, the infection is a resistant infection. In some aspects, the biophotonic compositions of this disclosure are for topical use.

In some other aspects, the disclosure provides for use of a biophotonic composition for the treatment of a patient afflicted with a skin or soft tissue wound having a non-resistant or a resistant infection or both categories of infection, wherein said composition comprises: at least one oxidant; and at least one chromophore capable of activating the oxidant; in association with a pharmacologically acceptable carrier. In certain such aspects, the soft tissue wound comprises an oral disease. In certain such aspects, the wound is a skin wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline or a canine. In certain such aspects, the infection is a resistant infection.

Biophotonic Compositions

The present disclosure provides methods and uses comprising biophotonic compositions for treating a skin or soft tissue wound having a non-resistant or a resistant infection or both categories of infection. Biophotonic compositions are compositions that are, in a broad sense, activated by light (e.g., photons) of specific wavelength. These compositions contain at least one exogenous chromophore which is activated by light and accelerates the dispersion of light energy, which leads to light carrying on a therapeutic effect on its own, and/or to the photochemical activation of other agents contained in the composition. The composition may comprise an agent which, when mixed with a chromophore or combination of chromophores and subsequently activated by light, can be photochemically activated which may lead to the formation of oxygen radicals, such as singlet oxygen. In some aspects, the disclosure provides a method of treating a resistant infection comprising: applying a biophotonic composition to a patient in need thereof, wherein the biophotonic composition comprises at least one oxidant and at least one chromophore capable of activating the oxidant; and exposing said biophotonic composition to actinic light for a time sufficient for said chromophore to cause activation of said oxidant.

When a chromophore absorbs a photon of a certain wavelength, it becomes excited. This is an unstable condition and the molecule tries to return to the ground state, giving away the excess energy. For some chromophores, it is favorable to emit the excess energy as light when transforming back to the ground state. This process is called fluorescence. The peak wavelength of the emitted fluorescence is shifted towards longer wavelengths compared to the absorption wavelengths ('Stokes' shift'). The emitted fluorescent energy can then be transferred to the other components of the composition or to a treatment site on to which the biophotonic composition is topically applied. Differing wavelengths of light may have different and complementary therapeutic effects on tissue. Stokes' shift is illustrated in FIG. 1.

Without being bound to theory, it is thought that fluorescent light emitted by photoactivated chromophores may have therapeutic properties due to its femto-, pico- or nano-second emission properties which may be recognized by biological cells and tissues, leading to favorable biomodulation. Furthermore, the emitted fluorescent light has a longer wavelength and hence a deeper penetration into the tissue than the activating light. Irradiating tissue with such a broad range of wavelengths, including in some embodiments the activating light which passes through the composition, may have different and complementary effects on the cells and tissues.

Moreover, in some embodiments of the composition containing oxidants, micro-bubbling within the composition has been observed which may be associated with the generation of oxygen species by the photoactivated chromophores. This may have a physical impact on the tissue to which it is applied, for example by dislodging biofilm and debridement of necrotic tissue or providing a pressure stimulation. The biofilm can also be pre-treated with an oxygen-releasing agent to weaken the biofilm before treating with the composition of the present disclosure.

In certain embodiments, the biophotonic compositions of the present disclosure are substantially transparent/translucent and/or have high light transmittance in order to permit light dissipation into and through the composition. In this way, the area of tissue under the composition can be treated both with the fluorescent light emitted by the composition and the light irradiating the composition to activate it, which may benefit from the different therapeutic effects of light having different wavelengths.

The percentage (%) transmittance of the biophotonic composition can be measured in the range of wavelengths from 250 nm to 800 nm using, for example, a Perkin-Elmer Lambda™ 9500 series UV-visible spectrophotometer. Alternatively, a Synergy™ HT spectrophotometer (BioTek Instrument, Inc.) can be used in the range of wavelengths from 380 nm to 900 nm.

Transmittance is calculated according to the following equation:

$$A_\lambda = \log_{10}\frac{I_0}{I} = \log_{10}\frac{1}{T}.$$

where A is absorbance, T is transmittance, $I_0$ is intensity of radiation before passing through material, and I is intensity of light passing through material.

The values can be normalized for thickness. As stated herein, % transmittance (translucency) is as measured for a 2 mm thick sample at a wavelength of 526 nm. It will be clear that other wavelengths can be used.

Embodiments of the biophotonic compositions of the present disclosure are for topical uses. The biophotonic composition can be in the form of a semi-solid or viscous liquid, such as a gel, or are gel-like, and which have a spreadable consistency at room temperature (e.g., about 20-25° C.), prior to illumination. By spreadable is meant that the composition can be topically applied to a treatment site at a thickness of less than about 0.5 mm, or from about 0.5 mm to about 3 mm, about 0.5 mm to about 2.5 mm, or about 1 mm to about 2 mm. In some embodiments, the composition can be topically applied to a treatment site at a thickness of about 2 mm or about 1 mm. Spreadable compositions can conform to a topography of a treatment site. This can have advantages over a non-conforming material in that a better and/or more complete illumination of the treatment site can be achieved and the compositions are easy to apply and remove.

These compositions may be described based on the components making up the composition. Additionally or alternatively, the compositions of the present disclosure have functional and structural properties and these properties may also be used to define and describe the compositions. Individual components of the composition of the present disclosure are detailed below.

Oxidants

In some embodiments, the biophotonic compositions of the present disclosure further comprise oxidants as a source of oxygen radicals. For instance, peroxide compounds are oxidants that contain the peroxy group (R—O—O—R), which is a chainlike structure containing two oxygen atoms, each of which is bonded to the other and a radical or some element. In some embodiments, the biophotonic compositions of this disclosure comprises an oxidant selected from, but not limited to, hydrogen peroxide, carbamide peroxide, benzoyl peroxide, peroxy acids, or alkali metal percarbonates.

Hydrogen peroxide ($H_2O_2$) is the starting material to prepare organic peroxides. $H_2O_2$ is a powerful oxidizing agent, and the unique property of hydrogen peroxide is that it breaks down into water and oxygen and does not form any persistent, toxic residual compound. Hydrogen peroxide for use in this composition can be used in a gel, for example with 6% hydrogen peroxide by weight of the composition. A suitable range of concentration over which hydrogen peroxide can be used in a composition of the present disclosure is less than about 12% by weight of the total compositions. In some embodiments, hydrogen peroxide is present in an amount from about 0.1% to about 12%, from about 1% to about 12%, from about 3.5% to about 12%, from about 3.5% to about 6% or from about 0.1% to about 6% by weight of the total composition.

Urea hydrogen peroxide (also known as urea peroxide, carbamide peroxide or percarbamide) is soluble in water and contains about 36% hydrogen peroxide. Carbamide peroxide for use in this composition can be used as a gel, for example with about 16% carbamide peroxide that represents about 5.6% hydrogen peroxide. A suitable range of concentration over which urea peroxide can be used in the present composition is less than about 36% by weight of the total composition. In some embodiments, urea peroxide is present in an amount from about 0.3% to about 36%, such as from about 3% to about 36%, from about 10% to about 36%, from about 3% to about 16%, from about 3% to about 9%, or from about 0.3% to about 16% by weight of the total composition. In some embodiments, urea peroxide is present in an amount of about 2% by weight of the total composition. In some embodiments, urea peroxide is present in an amount of about 3% by weight of the total composition. In some embodiments, urea peroxide is present in an amount of about 6% by weight of the total composition. In some embodiments, urea peroxide is present in an amount of about 8% by weight of the total composition. In some embodiments, urea peroxide is present in an amount of about 9% by weight of the total composition. In some embodiments, urea peroxide is present in an amount of about 12% by weight of the total composition. Urea peroxide breaks down to urea and hydrogen peroxide in a slow-release fashion that can be accelerated with heat or photochemical reactions. The released urea (i.e., carbamide, $(NH_2)_2CO$), is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. The released peroxide groups are effective as antibacterial agents. Benzoyl peroxide also promotes skin turnover and clearing of pores. Benzoyl peroxide breaks down to benzoic acid and oxygen upon contact with skin, neither of which is toxic. A suitable range of concentration over which benzoyl peroxide can be used in the present composition is less than about 10% by weight of the total composition. In some embodiments, benzoyl peroxide is present in an amount from about 1% to about 10%, or from about 1% to about 8%, or from about 2.5% to about 5% by weight of the total composition.

Suitable oxidants may also include peroxy acids and alkali metal percarbonates, but the inclusion of any other forms of peroxides (e.g., organic or inorganic peroxides) should be avoided due to their increased toxicity and their unpredictable reaction with the photodynamic energy transfer.

Chromophores/Photoactivators

In some embodiments, the biophotonic compositions of the present disclosure further comprise one or more chromophores, which can be considered exogenous, e.g., a chromophore that is not naturally present in skin or tissue. When a biophotonic composition of the present disclosure is illuminated with light, the chromophore(s) are excited to a higher energy state. When the chromophore(s)' electrons return to a lower energy state, they emit photons with a lower energy level, thus causing the emission of light of a longer wavelength (Stokes' shift). In the proper environment, some of this energy release is transferred to oxygen and causes the formation of oxygen radicals, such as singlet oxygen.

Suitable chromophores for the biophotonic compositions of the disclosure can be fluorescent dyes (or stains), although other dye groups or dyes (biological and histological dyes, food colorings, carotenoids, naturally occurring fluorescent and other dyes) can also be used.

In some embodiments, the biophotonic topical composition of the present disclosure comprises a chromophore which undergoes partial or complete photobleaching upon application of light. By photobleaching is meant a photochemical destruction of the chromophore which can generally be characterized as a loss of visual color or loss of fluorescence.

In some embodiments, the chromophore absorbs at a wavelength in the range of the visible spectrum, such as at a wavelength of about 380-800 nm, about 380-700 nm, or about 380-600 nm. In some embodiments, the chromophore absorbs at a wavelength of about 200-800 nm, about 200-700 nm, about 200-600 nm or about 200-500 nm. In some embodiments, the chromophore absorbs at a wavelength of about 200-600 nm. In some embodiments, the chromophore absorbs light at a wavelength of about 200-300 nm, about 250-350 nm, about 300-400 nm, about 350-450 nm, about 400-500 nm, about 400-600 nm, about 450-650 nm, about 600-700 nm, about 650-750 nm or about 700-800 nm.

In some embodiments, the chromophore or combination of chromophores is present in an amount of about 0.001-40% by weight of the total composition. In some embodiments, the chromophore or combination of chromophores is present in an amount of about 0.005-2%, about 0.01-1%, about 0.01-2%, about 0.05-1%, about 0.05-2%, about 0.1-1%, about 0.1-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the total composition. In some embodiments, the chromophore or combination of chromophores is present in an amount of at least about 0.2% by weight of the total composition.

In some embodiments, the chromophore or combination of chromophores is present in an amount of 0.001-40% by weight of the composition. In some embodiments, the chromophore or combination of chromophores is present in an amount of 0.005-2%, 0.01-1%, 0.01-2%, 0.05-1%, 0.05-2%, 0.1-1%, 0.1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the total composition. In some embodiments, the chromophore or combination of chromophores is present in an amount of at least 0.2% by weight of the total composition.

It will be appreciated to those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectra) measured in a biophotonic composition of the present disclosure.

In some embodiments, the biophotonic compositions disclosed herein may include at least one additional chromophore. Combining chromophores may increase photoabsorption by the combined dye molecules and enhance absorption and photo-biomodulation selectivity. This creates multiple possibilities of generating new photosensitive, and/or selective chromophores mixtures.

Figure 2:
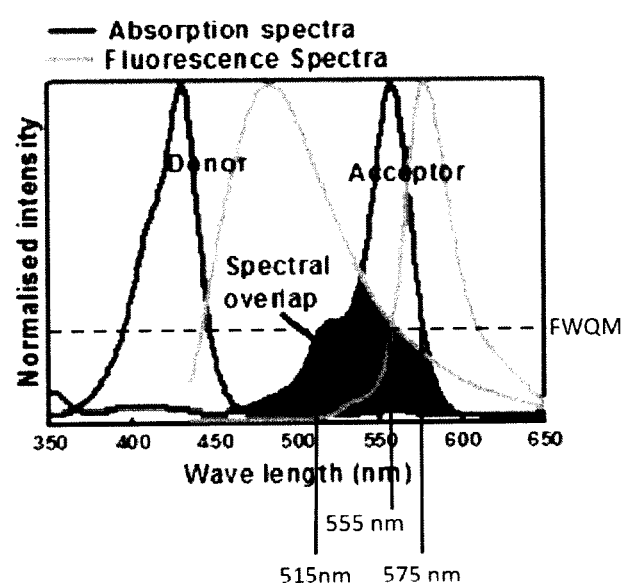
FIG. 2 illustrates the absorption and emission spectra of donor and acceptor chromophores. The spectral overlap between the absorption spectrum of the acceptor chromophore and the emission spectrum of the donor chromophore is also shown.

When such multi-chromophore compositions are illuminated with light, energy transfer can occur between the chromophores. This process, known as resonance energy transfer, is a photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. For energy transfer to occur the emission spectrum of the donor chromophore overlap with the absorption spectrum of the acceptor chromophore (FIG. 2).

Figure 3:
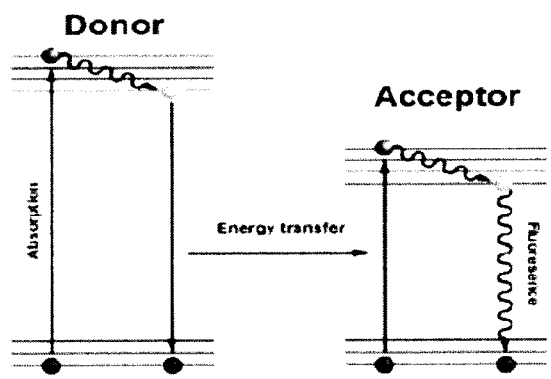
FIG. 3 is a schematic of a Jablonski diagram that illustrates the coupled transitions involved between a donor emission and acceptor absorbance.

Energy transfer manifests itself through decrease or quenching of the donor emission and a reduction of excited state lifetime accompanied also by an increase in acceptor emission intensity. FIG. 3 is a Jablonski diagram that illustrates the coupled transitions involved between a donor emission and acceptor absorbance.

To enhance the energy transfer efficiency, the donor chromophore should have good abilities to absorb photons and emit photons. Furthermore, it is thought that the more overlap there is between the donor chromophore's emission spectra and the acceptor chromophore's absorption spectra, the better a donor chromophore can transfer energy to the acceptor chromophore.

In some embodiments, the biophotonic topical composition of the present disclosure further comprises an acceptor, or a second, chromophore. In some embodiments, the donor, or first, chromophore has an emission spectrum that overlaps at least about 80%, about 70%, about 60%, about 50%, about 40%, about 30%, about 20%, or about 10% with an absorption spectrum of the second chromophore. In some embodiments, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

Percentage (%) spectral overlap, as used herein, means the % overlap of a donor chromophore's emission wavelength range with an acceptor chromophore's absorption wavelength range, measured at spectral full width quarter maximum (FWQM). For example, FIG. 2 shows the normalized absorption and emission spectra of donor and acceptor chromophores. The spectral FWQM of the acceptor chromophore's absorption spectrum is from about 60 nm (about 515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In some embodiments, the second chromophore has an absorption wavelength that is relatively longer than that of the first chromophore within the range of about 50-250 nm, about 25-150 nm or about 10-100 nm.

As discussed above, the application of light to the compositions of the present disclosure can result in a cascade of energy transfer between the chromophores. In some embodiments, such a cascade of energy transfer provides photons that penetrate the epidermis, dermis and/or mucosa of the target tissue, including, such as, a site of wound.

In some embodiments, the chromophore or chromophores are selected such that their emitted fluorescent light, on photoactivation, is within one or more of the green, yellow, orange, red and infrared portions of the electromagnetic spectrum, for example having a peak wavelength within the range of about 490 nm to about 800 nm. In some embodiments, the emitted fluorescent light has a power density of between 0.005 to about 10 mW/cm$^2$, about 0.5 to about 5 mW/cm$^2$.

Suitable chromophores useful in the biophotonic topical compositions, methods, and uses of the present disclosure include, but are not limited to the following:

Xanthene Derivatives

The xanthene derivative dyes have been used and tested for a long time worldwide. They display low toxicity and increased fluorescence. The xanthene group consists of three sub-groups: a) the fluorenes; b) fluorones; and c) the rhodoles, any of which may be suitable for the biophotonic compositions, methods, and uses of the present disclosure.

The fluorenes group comprises the pyronines (e.g., pyronine Y and B) and the rhodamines (e.g., rhodamine B. G and WT). Depending on the concentration used, both pyronines and rhodamines may be toxic and their interaction with light may lead to increased toxicity. Similar effects are known to occur for the rhodole dye group.

The fluorone group comprises the fluorescein dye and the fluorescein derivatives.

Fluorescein is a fluorophore commonly used in microscopy with an absorption maximum of about 494 nm and an emission maximum of about 521 nm. The disodium salt of fluorescein is known as D&C Yellow 8. It has very high fluorescence but photodegrades quickly. In the present composition, mixtures of fluorescein with other photoactivators such as indocyanin green and/or saffron red powder will confer increased photoabsorption to these other compounds.

The eosins group comprises Eosin Y (tetrabromofluorescein, acid red 87, D&C Red 22), a chromophore with an absorption maximum of about 514-518 nm that stains the cytoplasm of cells, collagen, muscle fibers and red blood cells intensely red; and Eosin B (acid red 91, eosin scarlet, dibromo-dinitrofluorescein), with the same staining characteristics as Eosin Y. Eosin Y and Eosin B are collectively referred to as "Eosin", and use of the term "Eosin" refers to either Eosin Y, Eosin B or a mixture of both. Eosin Y, Eosin B, or a mixture of both can be used because of their sensitivity to the light spectra used: broad spectrum blue light, blue to green light and green light. In some embodiments, the composition includes in the range of less than about 12% by weight of the total composition of at least one of Eosin B or Eosin Y or a combination thereof. In some embodiments, at least one of Eosin B or Eosin Y or a combination thereof is present from about 0.001% to about 12%, or between about 0.01% and about 1.2%, or from about 0.01% to about 0.5%, or from about 0.01% to about 0.05%, or from about 0.1% to about 0.5%, or from about 0.5% to about 0.8% by weight of the total composition. In some embodiments, at least one of Eosin B or Eosin Y or a combination thereof is present is an amount of at about 0.005% by weight of the total composition. In some embodiments, at least one of Eosin B or Eosin Y or a combination thereof is present is an amount of at about 0.01% by weight of the total composition.

In some embodiments, at least one of Eosin B or Eosin Y or a combination thereof is present is an amount of about 0.02% by weight of the total composition. In some embodiments, at least one of Eosin B or Eosin Y or a combination thereof is present is an amount of about 0.05% by weight of the total composition. In some embodiments, at least one of Eosin B or Eosin Y or a combination thereof is present is an amount of about 0.1% by weight of the total composition. In some embodiments, at least one of Eosin B or Eosin Y or a combination thereof is present is an amount of at about 0.2% by weight of the total composition. In some embodiments, at least one of Eosin B or Eosin Y or a combination thereof is present is an amount of at least about 0.2% by weight of the total composition but less than about 1.2% by weight of the total composition. In some embodiments, at least one of Eosin B or Eosin Y or a combination thereof is present is an amount of at least about 0.01% by weight of the total composition but less than about 12% by weight of the total composition.

In some embodiments, the composition includes in the range of less than 12% by weight of the total composition of at least one of Eosin B or Eosin Y or a combination thereof. In some embodiments, at least one of Eosin B or Eosin Y or a combination thereof is present from 0.001% to 12%, or between 0.01% and 1.2%, or from 0.01% to 0.5%, or from 0.1% to 0.5%, or from 0.5% to 0.8%, or from 0.01% to 0.05%, by weight of the total composition. In some embodiments, at least one of Eosin B or Eosin Y or a combination thereof is present is an amount of 0.005% by weight of the total composition. In some embodiments, at least one of Eosin B or Eosin Y or a combination thereof is present is an amount of 0.01% by weight of the total composition. In some embodiments, at least one of Eosin B or Eosin Y or a combination thereof is present is an amount of 0.02% by weight of the total composition. In some embodiments, at least one of Eosin B or Eosin Y or a combination thereof is present is an amount of 0.05% by weight of the total composition. In some embodiments, at least one of Eosin B or Eosin Y or a combination thereof is present is an amount of 0.1% by weight of the total composition. In some embodiments, at least one of Eosin B or Eosin Y or a combination thereof is present is an amount of 0.2% by weight of the total composition. In some embodiments, at least one of Eosin B or Eosin Y or a combination thereof is present is an amount of at least 0.2% by weight of the total composition but less than 1.2% by weight of the total composition. In some embodiments, at least one of Eosin B or Eosin Y or a combination thereof is present is an amount of at least 0.01% by weight of the total composition but less than 12% by weight of the total composition.

Phloxine B (2,4,5,7 tetrabromo 4,5,6,7,tetrachlorofluorescein, D&C Red 28, acid red 92) is a red dye derivative of fluorescein which is used for disinfection and detoxification of waste water through photooxidation. It has an absorption maximum of 535-548 nm. It is also used as an intermediate for making photosensitive dyes and drugs.

Erythrosine B, or simply Erythrosine or Erythrosin (acid red 51, tetraiodofluorescein) is a cherry-pink, coal-based fluorine food dye used as a biological stain, and a biofilm and dental plaque disclosing agent, with a maximum absorbance of 524-530 nm in aqueous solution. It is subject to photodegradation. Erythrosine is also used in some embodiments due to its photosensitivity to the light spectra used and its ability to stain biofilms. In embodiments, the composition includes in the range of less than about 2% by weight Erythrosine B. In some embodiments, Erythrosine B is present in an amount from about 0.005 to about 2%, or from 0.005% to about 1%, or about 0.01% to about 1% by weight of the total composition. In some embodiments, Erythrosine B is present in an amount of about 0.005% and about 0.15% by weight of the total composition.

Rose Bengal (4,5,6,7 tetrachloro 2,4,5,7 tetraiodofluorescein, acid red 94) is a bright bluish-pink fluorescein derivative with an absorption maximum of 544-549 nm, that has been used as a dye, biological stain and diagnostic aid. Rose Bengal is also used in synthetic chemistry to generate singlet oxygen from triplet oxygen.

Merbromine (mercurochrome) is an organo-mercuric disodium salt of fluorescein with an absorption maximum of 508 nm. It is used as an antiseptic.

Azo Dyes

The azo (or diazo-) dyes share the N—N group, called azo the group. They are used mainly in analytical chemistry or as food colorings and are not fluorescent. Suitable azo dyes for the compositions, methods, and uses of the disclosure include: Methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

Biological Stains

Dye molecules commonly used in staining protocols for biological materials can also be used as photoactivators for the compositions, methods, and uses of the disclosure. Suitable biological stains include, but not limited to, saffranin, fuchsin, 3,3'-dihexylocarbocyanine iodide, carminic acid, and indocyanin green.

Saffranin (Saffranin 0, basic red 2) is an azo-dye and is used in histology and cytology. It is a classic counter stain in a Gram stain protocol.

Fuchsin (basic or acid) (rosaniline hydrochloride) is a magenta biological dye that can stain bacteria and has been used as an antiseptic. It has an absorption maximum of 540-555 nm.

3,3'-dihexylocarbocyanine iodide (DiOC6) is a fluorescent dye used for staining the endoplasmic reticulum, vesicle membranes and mitochondria of cells. It shows photodynamic toxicity; when exposed to blue light, has a green fluorescence.

Carminic acid (acid red 4, natural red 4) is a red glucosidal hydroxyanthrapurin naturally obtained from cochineal insects.

Indocyanin green (ICG) is used as a diagnostic aid for blood volume determination; cardiac output, or hepatic function. ICG binds strongly to red blood cells and when used in mixture with fluorescein, it increases the absorption of blue to green light.

Carotenoids

Carotenoid dyes are also photoactivators that are useful in the compositions, methods, and uses of the disclosure.

Saffron red powder is a natural carotenoid-containing compound. Saffron is a spice derived from *crocus sativus*. It is characterized by a bitter taste and iodoform or hay-like fragrance; these are caused by the compounds picrocrocin and saffranal. It also contains the carotenoid dye crocin that gives its characteristic yellow-red color.

Saffron contains more than 150 different compounds, many of which are carotenoids: mangicrocin, reaxanthine, lycopene, and various α and β-carotenes, which show good absorption of light and beneficial biological activity. Also saffron can act as both a photon-transfer agent and a healing factor. Saffron color is primarily the result of a-crocin (8,8 diapo-8,8-carotenoid acid). Dry saffron red powder is highly sensitive to fluctuating pH levels and rapidly breaks down chemically in the presence of light and oxidizing agents. It is more resistant to heat. Data show that saffron has anti carcinogenic, immunomodulating and antioxidant properties. For absorbance, the crocin specific photon wavelength is 440 nm (blue light). It has a deep red colour and forms crystals with a melting point of 186° C. When dissolved in water, it forms an orange solution.

Crocetin, another compound of saffron, was found to express an antilipidemic action and promote oxygen penetration in different tissues. More specifically, an increased oxygenation of the endothelial cells of the capillaries was observed. Additionally, an increase of the oxygenation of muscles and cerebral cortex was observed and led to an improved survival rate in laboratory animals with induced hemorrhagic shock or emphysema.

Anatto, a spice, contains as main constituent (70-80%) the carotenoid bixin which displays relevant antioxidative properties. β-carotene, also displays suitable characteristics.

Fucoxanthine is a constituent of brown algae with a pronounced ability for photosensitization of redox reactions.

Chlorophyll Dyes

Exemplary chlorophyll dyes that are useful in the compositions, methods, and uses of the disclosure, include, but are not limited to, chlorophyll a, chlorophyll b, oil soluble chlorophyll, bacteriochlorophyll a, bacteriochlorophyll b, bacteriochlorophyll c, bacteriochlorophyll d, protochlorophyll, protochlorophyll a, amphiphilic chlorophyll derivative 1, and amphiphilic chlorophyll derivative 2.

In some aspects of the disclosure, the one or more chromophores of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin. Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2 (Saffranin 0), Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid (acid red 4), Celestine blue B, China blue, Cochineal, Celestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, DiOC6, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta 1, Magenta 11, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, phycobilins, Phycocyanins, Phycoerythrins. Phycoerythrincyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow 5, Swiss blue, Tartrazine, Thioflavine S. Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

Chromophores can be selected, for example, based on their emission wavelength properties in the case of fluorophores, on the basis of their energy transfer potential, their ability to generate reactive oxygen species, or their antimicrobial effect.

In some embodiments, the biophotonic compositions of the present disclosure comprise Eosin Y as a first chromophore. In some embodiments, the composition comprises Eosin Y as a first chromophore and any one or more of Rose Bengal, Erythrosin, Phloxine B as a second chromophore. It is believed that these combinations have a synergistic effect as Eosin Y can transfer energy to Rose Bengal, Erythrosin or Phloxine B when activated. This transferred energy is then emitted as fluorescence or by production of reactive oxygen species. This absorbed and re-emitted light is thought to be transmitted throughout the composition, and also to be transmitted into the site of treatment.

In some embodiments, the biophotonic compositions of this disclosure comprise the following synergistic combinations: Eosin Y and Fluorescein: Fluorescein and Rose Bengal; Erythrosine in combination with one or more of Eosin Y, Rose Bengal or Fluorescein; or Phloxine B in combination with one or more of Eosin Y, Rose Bengal, Fluorescein and Erythrosine. Other synergistic chromophore combinations may also be suitable for the biophotonic compositions of this disclosure.

By means of synergistic effects of the chromophore combinations in the composition, chromophores which cannot normally be activated by an activating light (such as a blue light from an LED) can be activated through energy transfer from chromophores which are activated by the activating light. In this way, the different properties of photoactivated chromophores can be harnessed and tailored according to the cosmetic or the medical therapy required.

For example, Rose Bengal can generate a high yield of singlet oxygen when photoactivated in the presence of molecular oxygen, however it has a low quantum yield in terms of emitted fluorescent light. Rose Bengal has a peak absorption at around 540 nm; so it is normally activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photoactivates Eosin Y which transfers some of its energy to Rose Bengal and emits some energy as fluorescence.

Chromophore combinations can also have a synergistic effect in terms of their photoactivated state. For example, two chromophores may be used, one of which emits fluorescent light when activated in the blue and green range, and the other which emits fluorescent light in the red, orange and yellow range, thereby complementing each other and irradiating the target tissue with a broad wavelength of light having different depths of penetration into target tissue and different therapeutic effects.

Healing Factors

According to some embodiments, the biophotonic compositions of the present disclosure may further comprise one or more healing factors. Healing factors include compounds that promote or enhance the healing or regenerative process of the tissues on the application site of the composition. During the photoactivation of the composition, there is an increase of the absorption of molecules at the treatment site. An augmentation in the blood flow at the site of treatment is observed for an extended period of time. An increase in the lymphatic drainage and a possible change in the osmotic equilibrium due to the dynamic interaction of the free radical cascades can be enhanced or even fortified with the inclusion of healing factors. In some embodiments, the biophotonic compositions of this disclosure comprises one or more healing factors selected from, but not limited to, hyaluronic acid, glucosamine, allantoin, or saffron.

Hyaluronic acid (hyaluronan or hyaluronate) is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissue hydrodynamics, movement and proliferation of cells and participates in a wide number of cell surface receptor interactions, notably those including primary receptor CD44. The hyaluronidase enzymes degrade hyaluronan, and there are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Current studies evidenced hyaluronic acid appearing in the early stages of healing to physically create room for white blood cells that mediate the immune response. It is used in the synthesis of biological scaffolds for wound healing applications and in wrinkle treatment. In certain embodiments, the composition includes hyaluronic acid in the range of less than about 2% by weight of the total composition hyaluronic acid. In some embodiments, hyaluronic acid is present in an amount from about 0.001% to about 2%, or from about 0.002% to about 2%, or from about 0.002% to about 1% by weight of the total composition.

Glucosamine is one of the most abundant monosaccharides in human tissues and a precursor in the biological synthesis of glycosylated proteins and lipids. It is commonly used in the treatment of osteoarthritis. The common form of glucosamine used is its sulfate salt. Glucosamine shows a number of effects, including anti-inflammatory activity, stimulation of the synthesis of proteoglycans and the synthesis of proteolytic enzymes. A suitable range of concentration over which glucosamine can be used in the present composition is from less than about 5% by weight of the total composition. In some embodiments, glucosamine is present in an amount from about 0.0001% to about 5%, or from about 0.0001% to about 3%, or from about 0.001% to about 3%, or from about 0.001% to about 1%, or from about 0.01% to about 1%, or from about 1% to about 3% by weight of the total composition.

Allantoin is a diureide of glyosilic acid. It has keratolytic effect, increases the water content of the extracellular matrix, enhances the desquamation of the upper layers of dead (apoptotic) skin cells, and promotes skin proliferation and wound healing. In certain embodiments, the composition includes in the range of less than about 1% by weight of the total composition allantoin. In some embodiments, allantoin is present in an amount of from about 0.001% to about 1%, or from about 0.002% to about 1%, or from about 0.02% to about 1%, or from about 0.02% to about 0.5% by weight of the total composition.

Saffron can act as both a photon-transfer agent and a healing factor.

Chelating Agents

According to some embodiments, the biophotonic compositions of the present disclosure may further comprise one or more chelating agents. Chelating agents can be included to promote smear layer removal in closed pockets and difficult to reach lesions. Chelating agents act as a metal ion quencher and as a buffer. In some embodiments, the biophotonic compositions of this disclosure comprise a chelating agent selected from, but not limited to, ethylenediaminotetraacetic acid or ethylene glycol tetraacetic acid.

Ethylenediaminotetraacetic acid (EDTA) is an amino acid and is used to sequester di- and trivalent metal ions. EDTA binds to metals via four carboxylate and two amine groups. EDTA forms especially strong complexes with Mn(III), Fe(III), Cu(III), Co(III). It is used to buffer solutions.

Ethylene glycol tetraacetic acid (EGTA) is related to EDTA, but with a much higher affinity for calcium than magnesium ions. It is useful for making buffer solutions that resemble the environment inside living cells.

Gelling Agents

According to some embodiments, the biophotonic compositions of the present disclosure may further comprise one or more gelling agents. The gelling agent may be an agent capable of forming a cross-linked matrix, including physical and/or chemical cross-links. The gelling agent can be biocompatible, and may be biodegradable. In some embodiments, the gelling agent is able to form a hydrogel or a hydrocolloid. An appropriate gelling agent is one that can form a viscous liquid or a semisolid. In some embodiments, the gelling agent and/or the composition has appropriate light transmission properties. It is also important to select a gelling agent which will allow biophotonic activity of the chromophore(s). For example, some chromophores require a hydrated environment in order to fluoresce. The gelling agent may be able to form a gel by itself or in combination with other ingredients such as water or another gelling agent, or when applied to a treatment site, or when illuminated with light.

The gelling agent according to various embodiments of the present disclosure may include, but not be limited to, polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly (methacrylamide), poly(dimethylacrylamide), and poly(N-isopropyl-acrylamide); poly(olefinic alcohol)s such as poly (vinyl alcohol); poly(N-vinyl lactams) such as poly(vinyl pyrrolidone), poly(N-vinyl caprolactam), and copolymers thereof, polyoxazolines, including poly(methyloxazoline) and poly(ethyloxazoline); silicones, polyvinyl silicates, tetramethoxyorthosilicates, methyltrimethoxyorthosilicates, tetraalkoxyorthosilicates, trialkoxyorthosilicates, pressure sensitive silicone adhesives (such as BioPSA from Dow-Corning), and polyvinylamines.

The gelling agent according to some embodiments of the present disclosure may include a polymer selected from any of synthetic or semi-synthetic polymeric materials, polyacrylate copolymers, cellulose derivatives and polymethyl vinyl ether/maleic anhydride copolymers. In some embodiments, the hydrophilic polymer comprises a polymer that is a high molecular weight (i.e., molar masses of more than about 5,000, and in some instances, more than about 10,000, or about 100,000, or about 1,000,000) and/or cross-linked polyacrylic acid polymer.

In some embodiments, the gelling agent comprises a carbomer. Carbomers are synthetic high molecular weight polymer of acrylic acid that are cross-linked with either allylsucrose or allylethers of pentaerythritol having a molecular weight of about $3 \times 10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

Carbomers are available as fine white powders which disperse in water to form acidic colloidal suspensions (a 1% dispersion has a pH of approximately 3) of low viscosity. Neutralization of these suspensions using a base, for example sodium, potassium or ammonium hydroxides, low molecular weight amines and alkanolamines, results in the formation of translucent gels. Nicotine salts such as nicotine chloride form stable water-soluble complexes with carbomers at about pH 3.5 and are stabilized at an optimal pH of about 5.6.

In some embodiments of the disclosure, the carbomer is Carbopol®. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In some embodiments, the carbomer is Carbopol® 980 NF, ETD 2020 NF, Ultrez 10 NF, Ultrez 21 or 1382 Polymer, 1342 NF, 940 NF. In some embodiments, from about 0.05% to about 10%, about 0.5% to about 5%, or about 1% to about 3% by weight of the total composition of a high molecular weight carbopol can be present as the gelling agent. In some embodiments, the biophotonic composition of the disclosure comprises from about 0.05% to about 10%, about 0.5% to about 5%, or from about 1% to about 3% by weight of the total composition of a high molecular weight carbopol.

In some embodiments, the gelling agent comprises a hygroscopic and/or a hydrophilic material useful for their water attracting properties. The hygroscopic or hydrophilic material may include, but is not limited to, glucosamine, glucosamine sulfate, polysaccharides, cellulose derivatives (hydroxypropyl methylcellulose, hydroxyethyl cellulose, hydroxypropyl cellulose, methylcellulose and the like), non-cellulose polysaccharides (galactomannans, guar gum, carob gum, gum arabic, sterculia gum, agar, alginates and the like), glycosaminoglycan, poly(vinyl alcohol), poly(2-hydroxyethylmethylacrylate), polyethylene oxide, collagen, chitosan, alginate, a poly(acrylonitrile)-based hydrogel, poly(ethylene glycol)/poly(acrylic acid) interpenetrating polymer network hydrogel, polyethylene oxide-polybutylene terephthalate, hyaluronic acid, high-molecular-weight polyacrylic acid, poly(hydroxy ethylmethacrylate), poly(ethylene glycol), tetraethylene glycol diacrylate, polyethylene glycol methacrylate, and poly(methyl acrylate-co-hydroxyethyl acrylate). In some embodiments, the hydrophilic gelling agent is selected from glucose, modified starch, methyl cellulose, carboxymethyl cellulose, propyl cellulose, hydroxypropyl cellulose, carbomers, alginic acid, sodium alginate, potassium alginate, ammonium alginate, calcium alginate, agar, carrageenan, locust bean gum, pectin, and gelatin.

The gelling agent may be protein-based/naturally derived material such as sodium hyaluronate, gelatin or collagen, lipids, or the like. The gelling agent may be a polysaccharide such as starch, chitosan, chitin, agarose, agar, locust bean gum, carrageenan, gellan gum, pectin, alginate, xanthan, guar gum, and the like.

In some embodiments, the composition can include up to about 2% by weight of the final composition of sodium hyaluronate as the single gelling agent. In some embodiments, the composition can include more than about 4% or more than about 5% by weight of the total composition of gelatin as the single gelling agent. In some embodiments, the composition can include up to about 10% or up to about 8% starch as the single gelling agent. In some embodiments, the composition can include more than about 5% or more than about 10% by weight of the total composition of collagen as the gelling agent. In some embodiments, about 0.1% to about 10% or about 0.5% to about 3% by weight of the total composition of chitin can be used as the gelling agent. In some embodiments, about 0.5% to about 5% by weight of the final composition of corn starch or about 5% to about 10% by weight of the total composition of corn starch can be used as the gelling agent. In some embodiments, more than about 2.5% by weight of the total composition of alginate can be used in the composition as the gelling agent. In some embodiments, the percentages by weight percent of the final composition of the gelling agents can be as follows: cellulose gel (from about 0.3% to about 2.0%), konjac gum (from about 0.5% to about 0.7%), carrageenan gum (from about 0.02% to about 2.0%), xanthan gum (from about 0.01% to about 2.0%), acacia gum (from about 3% to about 30%), agar (from about 0.04% to about 1.2%), guar gum (from about 0.1% to about 1%), locust bean gum (from about 0.15% to about 0.75%), pectin (from about 0.1% to about 0.6%), tara gum (from about 0.1% to about 1.0%), polyvinylypyrrolidone (from about 1% to about 5%), sodium polyacrylate (from about 1% to about 10%). Other gelling agents can be used in amounts sufficient to gel the composition or to sufficiently thicken the composition. It will be appreciated that lower amounts of the above gelling agents may be used in the presence of another gelling agent or a thickener.

In some embodiments, the biophotonic compositions of the present disclosure may be further encapsulated, e.g., in a membrane. Such a membrane may be transparent, and/or substantially, or fully impermeable. The membrane may be impermeable to liquid but permeable to gases such as air. In some embodiments, the composition may form a membrane that encapsulates the chromophore(s) of the biophotonic topical composition, where the membrane may be substantially impermeable to liquid and/or gas. The membrane may be formed of one or more lipidic agents, polymers, gelatin, cellulose or cyclodextrins, or the like. In some embodiments, the membrane is translucent or transparent to allow light to infiltrate to and from the chromophore(s). In some embodiments, the composition is a dendrimer with an outer membrane comprising poly(propylene amine). In some embodiments, the outer membrane comprises gelatin.

Polyols

According to some embodiments, the biophotonic compositions of the present disclosure may optionally further comprise one or more polyols. Suitable polyols that may be included in the composition include, but are not limited to a diol, a triol, a saccharide, glycerine, butane-1,2,3-triol, butane-1,2,4-triol, hexane-1,2,6-triol, propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol. In some embodiments when the biophotonic composition of the disclosure includes one or more polyols, the polyol is glycerine. In some embodiments when the biophotonic composition of the disclosure includes one or more polyols, the polyol is propylene glycol. In some embodiments when the biophotonic composition of the disclosure includes one or more polyols, the polyol is a combination of glycerine and propylene glycol.

In some embodiments, one or more polyols are present in an amount of about 5-75% by weight of the total composition, such as 5-75% by weight of the total composition. In some embodiments, one or more polyols are present in an amount of about 10-75% by weight of the total composition, such as 10-75% by weight of the total composition. In some embodiments, one or more polyols are present in an amount of about 15-75% by weight of the total composition, such as 15-75% by weight of the total composition. In some embodiments, one or more polyols are present in an amount of about 20-75% by weight of the total composition, such as 20-75% by weight of the total composition.

Antimicrobials

According to some embodiments, the biophotonic compositions of the present disclosure may optionally further comprise one or more antimicrobials. Antimicrobials are useful in reducing microbial growth or accumulation. Exemplary antimicrobials (or antimicrobial agent) are recited in U.S. Patent Application Publication Nos. 20040009227 and 20110081530. Suitable antimicrobials for use in the methods of the present disclosure include, but not limited to, phenolic and chlorinated phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic antimicrobial agents that can be used in the disclosure include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenyl; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5-dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2-methylphenol; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antimicrobial agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heplyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2,4-dihydroxydiphenyl methane.

Specific bisphenolic antimicrobial agents that can be used in the disclosure include, but are not limited to: 2,2'-methylene bis-(4-chlorophenol); 2,4,4'trichloro-2'-hydroxydiphenyl ether, which is sold by Ciba Geigy, Florham Park, N.J. under the trade name Triclosan®; 2,2'-methylene bis-(3,4,6-trichlorophenol); 2,2'-methylene bis-(4-chloro-6-bromophenol); bis-(2-hydroxy-3,5-dichlorophenyl)sulphide; and bis-(2-hydroxy-5-chlorobenzyl)sulphide.

Specific benzoic esters (parabens) that can be used in the disclosure include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used in the disclosure include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide.

Specific polymeric antimicrobial agents that can be used in the disclosure include, but are not limited to: polyhexamethylene biguanide hydrochloride; and poly(iminoimidocarbonyl iminoimidocarbonyl iminohexamethylene hydrochloride), which is sold under the tradename Vantocil® IB.

Specific thazolines that can be used in the disclosure include, but are not limited to that sold under the tradename Micro-Check®; and 2-n-octyl-4-isothiazolin-3-one, which is sold under the tradename Vinyzene® IT-3000 DIDP.

Specific trichloromethylthioimides that can be used in the disclosure include, but are not limited to: N-(trichloromethylthio)phthalimide, which is sold under the tradename Fungitrol®; and N-tnchloromethylthio-4-cyclohexene-1,2-dicarboximide, which is sold under the tradename Vancide®.

Specific natural antimicrobial agents that can be used in the disclosure include, but are not limited to, oils of: anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, honey, fennel, fir, balsam, menthol, ocmea origanuin, hydastis, carradensis, Berberidaceac daceae, Ratanhiae longa, and Curcuma longa. Also included in this class of natural antimicrobial agents are the key chemical components of the plant oils which have been found to provide antimicrobial benefit. These chemicals include, but are not limited to: anethol, catechole, camphene, thymol, eugenol, eucalyptol, ferulic acid, farnesol, hinokitiol, tropolone, limonene, menthol, methyl salicylate, carvacol, terpineol, verbenone, berberine, ratanhiae extract, caryophellene oxide, citronellic acid, curcumin, nerolidol, and geraniol.

Specific metal salts that can be used in the disclosure include, but are not limited to, salts of metals in Groups 3a-5a, 3b-7b, and 8 of the periodic table. Specific examples of metal salts include, but are not limited to, salts of aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thalium, ytterbium, lutetium, and mixtures thereof. An example of the metal-ion based antimicrobial agent is sold under the tradename HealthShield®, and is manufactured by HealthShield Technology, Wakefield, Mass.

Specific broad-spectrum antimicrobial agents that can be used in the disclosure include, but are not limited to, those that are recited in other categories of antimicrobial agents herein.

Additional antimicrobial agents that can be used in the methods of the disclosure include, but are not limited to: pyrithiones, and in particular pyrithione-including zinc complexes such as these sold under the tradename Octopirox®; dimethyidimethylol hydantoin, which is sold under the tradename Glydant®; methylchloroisothiazolinone/methylisothiazolinone, which is sold under the tradename Kathon CG®; sodium sulfite; sodium bisulfate; imidazolidinyl urea, which is sold under the tradename Germall 115®; diazolidinyl urea, which is sold under the tradename Germall 11®; benzyl alcohol v2-bromo-2-nitropropane-1,3-diol, which is sold under the tradename Bronopol®; formalin or formaldehyde; iodopropenyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

Additional antimicrobial agents that can be used in the methods of the disclosure include those disclosed by U.S. Pat. Nos. 3,141,321; 4,402,959; 4,430,381; 4,533,435; 4,625,026; 4,736,467; 4,855,139; 5,069,907; 5,091,102; 5,639,464; 5,853,883; 5,854,147; 5,894,042; and 5,919,554, and U.S. Pat. Appl. Publ. Nos. 20040009227 and 20110081530, the contents of all of which are incorporated herein by reference.

Collagens and Agents that Promote Collagen Synthesis

According to some embodiments, the biophotonic compositions of the present disclosure may optionally further comprise one or more collagens and/or agents that promote collagen synthesis. Collagen is a fibrous protein produced in dermal fibroblast cells and forming 70% of the dermis and benefits all stages of the wound healing process. Thus, collagens and agents that promote collagen synthesis may also be useful in the present disclosure. Agents that promote collagen synthesis (i.e., pro-collagen synthesis agents) include amino acids, peptides, proteins, lipids, small chemical molecules, natural products and extracts from natural products.

For instance, it was discovered that intake of vitamin C, iron, and collagen can effectively increase the amount of collagen in skin or bone. See, e.g., U.S. Patent Application Publication 20090069217, the contents of which are all incorporated herein by reference. Examples of the vitamin C include an ascorbic acid derivative such as L-ascorbic acid or sodium L-ascorbate, an ascorbic acid preparation obtained by coating ascorbic acid with an emulsifier or the like, and a mixture containing two or more of those vitamin Cs at an arbitrary rate. In addition, natural products containing vitamin C such as acerola and lemon may also be used. Examples of the iron preparation include: an inorganic iron such as ferrous sulfate, sodium ferrous citrate, or ferric pyrophosphate; an organic iron such as heme iron, ferritin iron, or lactoferrin iron; and a mixture containing two or more of those irons at an arbitrary rate. In addition, natural products containing iron such as spinach or liver may also be used. Moreover, examples of the collagen include: an extract obtained by treating bone, skin, or the like of a mammal such as bovine or swine with an acid or alkaline; a peptide obtained by hydrolyzing the extract with a protease such as pepsin, trypsin, or chymotrypsin; and a mixture containing two or more of those collagens at an arbitrary rate. Collagens extracted from plant sources may also be used.

Additional pro-collagen synthesis agents are described, for example, in U.S. Pat. Nos. 7,598,291, 7,722,904, 6,203, 805, 5,529,769, etc., and U.S. Patent Application Publications 20060247313, 20080108681, 20110130459, 20090325885, and 20110086060, the contents of all of which are incorporated herein by reference.

Additional Components

In some embodiments, the compositions of the disclosure can also include other ingredients such as humectants (e.g., glycerine, ethylene glycol, and propylene glycol), preservatives such as parabens, and pH adjusters such as sodium hydroxide, sodium bicarbonate, and HCl. In some embodiments, the pH of the composition is in or adjusted to the range of about 4 to about 10. In some embodiments, the pH of the composition is in or adjusted to the range of about 4 to about 9. In some embodiments, the pH of the composition is in or adjusted to the range of from about 4 to about 8. In some embodiments, the pH of the composition is within the range of from about 4 to about 7. In some embodiments, the pH of the composition is within the range of from about 4 to about 6.5. In some embodiments, the pH of the composition is within the range of from about 4 to about 6. In some embodiments, the pH of the composition is within the range of from about 4 to about 5.5. In some embodiments, the pH of the composition is within the range of from about 4 to about 5. In some embodiments, the pH of the composition is within the range of from about 5.0 to about 8.0. In some embodiments, the pH of the composition is within the range of from about 6.0 to about 8.0. In some embodiments, the pH of the composition is within the range of from about 6.5 to about 7.5. In some embodiments, the pH of the composition is within the range of from about 5.5 to about 7.5.

In some embodiments, the pH of the composition is in or adjusted to the range of 4 to 10. In some embodiments, the pH of the composition is in or adjusted to the range of 4 to 9. In some embodiments, the pH of the composition is in or adjusted to the range of 4 to 8. In some embodiments, the pH of the composition is within the range of 4 to 7. In some embodiments, the pH of the composition is within the range of 4 to 6.5. In some embodiments, the pH of the composition is within the range of 4 to 6. In some embodiments, the pH of the composition is within the range of 4 to 5.5. In some embodiments, the pH of the composition is within the range of 4 to 5. In some embodiments, the pH of the composition is within the range of 5.0 to 8.0. In some embodiments, the pH of the composition is within the range of 6.0 to 8.0. In some embodiments, the pH of the composition is within the range of 6.5 to 7.5. In some embodiments, the pH of the composition is within the range of 5.5 to 7.5.

In some embodiments, the biophotonic compositions of the disclosure also include an aqueous substance (such as water) or an alcohol. Alcohols include, but are not limited to, ethanol, propanol, isopropanol, butanol, iso-butanol, t-butanol or pentanol. In some embodiments, the chromophore or combination of chromophores is in solution in a medium of the biophotonic composition. In some embodiments, the chromophore or combination of chromophores is in solution in a medium of the biophotonic composition, wherein the medium is an aqueous substance.

Methods of Use and Treatment

Photoactivation

The biophotonic compositions suitable for use in the methods of the present disclosure may be selected from any of the embodiments of the biophotonic compositions described above. For instance, the biophotonic compositions useful in the method of the present disclosure may comprise a chromophore that undergoes at least partial photobleaching upon application of light. The chromophore may absorb at a wavelength of about from 200 nm to about 800 nm, such as from about 200 nm to about 700 nm, from about 200 nm to about 600 nm or from about 200 nm to about 500 nm. In some embodiments, the chromophore absorbs at a wavelength of about from 200 nm to about 600 nm. In some embodiments, the chromophore absorbs light at a wavelength of from about 200 nm to about 300 nm, from about 250 nm to about 350 nm, from about 300 nm to about 400 nm, from about 350 nm to about 450 nm, from about 400 nm to about 500 nm, from about 450 nm to about 650 nm, from about 600 nm to about 700 nm, from about 650 nm to about 750 nm or from about 700 nm to about 800 nm. In some embodiments, suitable biophotonic compositions for the methods of the present disclosure may further comprise at least one additional chromophore (e.g., a second chromophore). The absorption spectrum of the second chromophore overlaps at least about 80%, about 70%, about 60%, about 50%, about 40%, about 30%, or about 20% with the emission spectrum of the first chromophore. In some embodiments, the first chromophore has an emission spectrum that overlaps at least about 1-10%, about 5-15%, about 10-20%, about 15-25%, about 20-30%, about 25-35%, about 30-40%, about 35-45%, about 50-60%, about 55-65% or about 60-70% with an absorption spectrum of the second chromophore.

In the methods of the present disclosure, any source of actinic light can be used to illuminate the biophotonic compositions. Any type of halogen, LED or plasma arc lamp or laser may be suitable. The primary characteristic of suitable sources of actinic light will be that they emit light in a wavelength (or wavelengths) appropriate for activating the one or more photoactivators present in the composition. In some embodiments, an argon laser is used. In some embodiments, a potassium-titanyl phosphate (KTP) laser (e.g., a GreenLight™ laser) is used. In another embodiment, sunlight may be used. In some embodiments, a LED photocuring device is the source of the actinic light. In some embodiments, the source of the actinic light is a source of light having a wavelength between about 200 nm and about 800 nm. In some embodiments, the source of the actinic light is a source of visible light having a wavelength between about 400 nm and about 700 nm. In some embodiments, the source of the actinic light is a source of visible light having a wavelength between about 400 nm and about 600 nm. In some embodiments, the source of the actinic light is a source of visible light having a wavelength between about 400 nm and about 550 nm. In some embodiments, the source of the actinic light is a source of visible light having a wavelength between about 380 nm and about 700 nm. In some embodiments, the source of the actinic light is a source of visible light having a wavelength between about 380 nm and about 600 nm. In some embodiments, the source of the actinic light is a source of visible light having a wavelength between about 380 nm and about 550 nm. In some embodiments, the source of the actinic light is a source of visible light having a wavelength between about 380 nm and about 550 nm. In some embodiments, the source of the actinic light is a source of light having a wavelength between 200 nm to 800 nm. In some embodiments, the source of the actinic light is a source of visible light having a wavelength between 400 nm and 700 nm. In some embodiments, the source of the actinic light is a source of visible light having a wavelength between 400 nm and 600 nm. In some embodiments, the source of the actinic light is a source of visible light having a wavelength between 400 nm and 550 nm. In some embodiments, the source of the actinic light is a source of visible light having a wavelength between 380 nm and 700 nm. In some embodiments, the source of the actinic light is a source of visible light having a wavelength between 380 nm and 600 nm. In some embodiments, the source of the actinic light is a source of visible light having a wavelength between 380 nm and 550 nm. In some embodiments, the biophotonic composition of the disclosure is illuminated with violet and/or blue light. Furthermore, the source of actinic light should have a suitable power density. Suitable power density for non-collimated light sources (LED, halogen or plasma lamps) are in the range from about 1 mW/cm$^2$ to about 1200 mW/cm$^2$, such as from about 20 mW/cm$^2$ to about 1000 mW/cm$^2$ from about 100 mW/cm$^2$ to about 900 mW/cm$^2$ from about 200 mW/cm$^2$ to about 800 mW/cm$^2$, or from about 1 mW/cm$^2$ to about 200 mW/cm$^2$. In some embodiments, the power density for non-collimated light sources (LED, halogen or plasma lamps) are in the range from about 1 mW/cm$^2$ to about 200 mW/cm$^2$. Suitable power density for laser light sources is in the range from about 0.5 mW/cm$^2$ to about 0.8 mW/cm$^2$.

In some embodiments of the methods of the present disclosure, the light has an energy at the patient's skin of from about 1 mW/cm$^2$ to about 500 mW/cm$^2$, or about 1 mW/cm$^2$ to about 300 mW/cm$^2$, or about 1 mW/cm$^2$ to about 200 mW/cm$^2$, wherein the energy applied depends at least on the condition being treated, the wavelength of the light, the distance of the patient's skin from the light source, and the thickness of the biophotonic composition. In some embodiments, the light at the patient's skin is from about 1 mW/cm$^2$ to about 40 mW/cm$^2$, or about 20 mW/cm$^2$ to about 60 mW/cm$^2$, or about 40 mW/cm$^2$ to about 80 mW/cm$^2$, or about 60 mW/cm$^2$ to about 100 mW/cm$^2$, or about 80 mW/cm$^2$ to about 120 mW/cm$^2$, or about 100 mW/cm$^2$ to about 140 mW/cm$^2$, or about 120 mW/cm$^2$ to about 160 mW/cm$^2$, or about 140 mW/cm$^2$ to about 180 mW/cm$^2$, or about 160 mW/cm$^2$ to about 200 mW/cm$^2$, or about 110 mW/cm$^2$ to about 240 mW/cm$^2$, or about 110 mW/cm$^2$ to about 150 mW/cm$^2$, or about 190 mW/cm$^2$ to about 240 mW/cm$^2$.

In some embodiments, a mobile device can be used to activate embodiments of the biophotonic composition of the present disclosure, wherein the mobile device can emit light having an emission spectrum which overlaps an absorption spectrum of the chromophore in the biophotonic composition. The mobile device can have a display screen through which the light is emitted and/or the mobile device can emit light from a flashlight which photoactivates the biophotonic composition.

In some embodiments, a display screen on a television or a computer monitor can be used to activate the biophotonic composition, wherein the display screen can emit light having an emission spectrum which overlaps an absorption spectrum of a photoactive agent in the photoactivatable composition.

In some embodiments, the chromophore or combination of chromophores can be photoactivated by ambient light which may originate from the sun or other light sources. Ambient light can be considered to be a general illumination that comes from all directions in a room that has no visible source. In some embodiments, the chromophore or combination of chromophores can be photoactivated by light in the visible range of the electromagnetic spectrum. Exposure times to ambient light may be longer than that to direct light.

In some embodiments, different sources of light can be used to activate the biophotonic compositions, such as a combination of ambient light and direct LED light.

The duration of the exposure to actinic light required will be dependent on the surface of the treated area, the severity of the condition that is being treated, the power density, wavelength and bandwidth of the light source, the thickness of the biophotonic composition, and the treatment distance from the light source. The illumination of the treated area by fluorescence may take place within seconds or even fragment of seconds, but a prolonged exposure period is beneficial to exploit the synergistic effects of the absorbed, reflected and reemitted light on the composition of the present disclosure and its interaction with the tissue being treated. In some embodiments, the time of exposure to actinic light of the tissue or skin or wound on which the biophotonic composition has been applied is a period from about 1 second to about 30 minutes. In some embodiments, the time of exposure to actinic light of the tissue or skin or wound on which the biophotonic composition has been applied is a period from about 1 minute to about 30 minutes. In some embodiments, the time of exposure to actinic light of the tissue, skin or wound on which the biophotonic composition has been applied is a period from about 1 minute to about 5 minutes. In some embodiments, the time of exposure to actinic light of the tissue, skin or wound on which the biophotonic composition has been applied is a period between 1 minute to about 5 minutes. In another embodiment, the time of exposure is from about 20 seconds to about 5 minutes, or from about 60 seconds to about 5 minutes. In another embodiment, the time of exposure to actinic light of the tissue on which the biophotonic composition has been applied is a period of less than about 5 minutes. In another embodiment, the time of exposure is between about 20 seconds to about 5 minutes, or from about about 60 seconds to about 5 minutes per $cm^2$ of the area to be treated, so that the total time of exposure of a 10 $cm^2$ area would be from about 10 minutes to about 50 minutes.

In some embodiments, the biophotonic composition is illuminated for a period from about 1 minute and 3 minutes. In some embodiments, light is applied for a period of from about 1 to about 30 seconds, from about 1 second to about 60 seconds, from about 15 seconds to about 45 seconds, from about 30 seconds to about 60 seconds, from about 0.75 minute to about 1.5 minutes, from about 1 minute to about 2 minutes, from about 1.5 minutes to about 2.5 minutes, from about 2 minutes to about 3 minutes, from about 2.5 minutes to about 3.5 minutes, from about 3 minutes to about 4 minutes, from about 3.5 minutes to about 4.5 minutes, from about 4 minutes to about 5 minutes, from about 5 minutes to about 10 minutes, from about 10 minutes to about 15 minutes, from about 15 minutes to about 20 minutes, from about 20 minutes to about 25 minutes, or from about 20 minutes to about 30 minutes. In some embodiments, light is applied for a period of 1 second. In some embodiments, light is applied for a period of about 5 seconds. In some embodiments, light is applied for a period of about 10 seconds. In some embodiments, light is applied for a period of about 20 seconds. In some embodiments, light is applied for a period of about 30 seconds. In some embodiments, the biophotonic composition is illuminated for a period less than about 30 minutes. In some embodiments, the biophotonic composition is illuminated for a period less than about 20 minutes. In some embodiments, the biophotonic composition is illuminated for a period less than about 15 minutes. In some embodiments, the biophotonic composition is illuminated for a period less than about 10 minutes. In some embodiments, the biophotonic composition is illuminated for a period less than about 5 minutes. In some embodiments, the biophotonic composition is illuminated for a period less than about 1 minute. In some embodiments, the biophotonic composition is illuminated for a period less than about 30 seconds. In some embodiments, the biophotonic composition is illuminated for a period less than about 20 seconds. In some embodiments, the biophotonic composition is illuminated for a period less than 10 seconds. In some embodiments, the biophotonic composition is illuminated for a period less than 5 seconds. In some embodiments, the biophotonic composition is illuminated for a period less than 1 second. In some embodiments, the source of actinic light is in continuous motion over the treated area for the appropriate time of exposure. In some embodiments, multiple applications of the biophotonic composition and actinic light are performed. In some embodiments, the tissue, skin or wound is exposed to actinic light at least two, three, four, five or six times. In some embodiments, the tissue, skin or wound is exposed to actinic light at least two, three, four, five or six times with a resting period in between each exposure. In certain such embodiments, the resting period is less than about 1 minute, less than about 5 minutes, less than about 10 minutes, less than about 20 minutes, less about 40 minutes, less than about 60 minutes, less than about 2 hours, less than about 4 hours, less than about 6 hours, or less than 12 hours. In some embodiments, the entire treatment may be repeated in its entirety as may be required by the patient. In some embodiments, a fresh application of the biophotonic composition is applied before another exposure to actinic light.

In the methods of the present disclosure, the biophotonic composition may be optionally removed from the site of treatment following application of light. In some embodiments, the biophotonic composition is left on the treatment site for more than about 30 minutes, more than one hour, more than about 2 hours, or more than about 3 hours. It can be illuminated with ambient light. To prevent drying, the composition can be covered with a transparent or translucent cover such as a polymer film, or an opaque cover which can be removed before illumination.

The biophotonic compositions of the disclosure may be applied at regular intervals such as once a week, or at an interval deemed appropriate by the physician or veterinarian. In some embodiments, the biophotonic compositions of the disclosure are applied once per week for one or more weeks, such as once per week for one week. In some embodiments, the biophotonic compositions of the disclosure are applied once per week for two weeks. In some embodiments, the biophotonic compositions of the disclosure are applied once per week for three weeks. In some embodiments, the biophotonic compositions of the disclosure are applied once per week for four weeks. In some embodiments, the biophotonic compositions of the disclosure are applied once per week for five weeks. In some embodiments, the biophotonic compositions of the disclosure are applied once per week for six weeks. In some embodiments, the biophotonic compositions of the disclosure are applied once per week for seven weeks. In some embodiments, the biophotonic compositions of the disclosure are applied once per week for eight or more weeks.

In some embodiments, the biophotonic compositions of the disclosure are applied twice per week for one or more weeks, such as twice per week for one week. In some embodiments, the biophotonic compositions of the disclosure are applied twice per week for two weeks. In some embodiments, the biophotonic compositions of the disclosure are applied twice per week for three weeks. In some embodiments, the biophotonic compositions of the disclosure are applied twice per week for four weeks. In some embodiments, the biophotonic compositions of the disclosure are applied twice per week for five weeks. In some embodiments, the biophotonic compositions of the disclosure are applied twice per week for six weeks. In some embodiments, the biophotonic compositions of the disclosure are applied twice per week for seven weeks. In some embodiments, the biophotonic compositions of the disclosure are applied twice per week for eight or more weeks.

In some embodiments, the biophotonic compositions of the disclosure are applied three times or more per week for one or more weeks, such as three times or more for one week. In some embodiments, the biophotonic compositions of the disclosure are applied three times or more per week for two weeks. In some embodiments, the biophotonic compositions of the disclosure are applied three times or more per week for three weeks. In some embodiments, the biophotonic compositions of the disclosure are applied three times or more per week for four weeks. In some embodiments, the biophotonic compositions of the disclosure are applied three times or more per week for five weeks. In some embodiments, the biophotonic compositions of the disclosure are applied three times or more per week for six weeks. In some embodiments, the biophotonic compositions of the disclosure are applied three times or more per week for seven weeks. In some embodiments, the biophotonic compositions of the disclosure are applied three times or more per week for eight or more weeks.

For any of the methods described herein, the embodiments of this disclosure contemplate the use of any of the compositions, or mixtures of them, described throughout the application. In addition, in various embodiments of any of the methods described herein, combinations of any step or steps of one method with any step or steps from another method may be employed.

Resistant Infections

The biophotonic compositions of the present disclosure have numerous uses. In some embodiments, the biophotonic compositions of the present disclosure are useful in the treatment of resistant infections. A resistant infection is an infection caused by a microorganism that is resistant to an antimicrobial or anti-infective agent that was originally effective for treatment of infections caused by it. Resistant microorganisms (including bacteria, fungi, viruses and parasites) are able to withstand treatment by antimicrobial or anti-infective agents, such as antibacterial agents (e.g., antibiotics), antifungals, antivirals, and antiprotozoals, so that standard treatments become ineffective and infections persist. As resistant infections fail to respond to standard treatments, they result in prolonged illness and/or healing, reduced effectiveness of treatment, higher health care expenditures, and a greater risk of death. In some embodiments wherein the present disclosure provides biophotonic compositions and methods for treating and/or preventing resistant infections, the resistant infection is a bacterial infection. In certain such embodiments wherein the resistant infection is a bacterial infection, the bacterial infection is resistant to antibiotics.

The present disclosure provides biophotonic compositions and methods for treating a resistant infection, wherein the resistant infection is present on a mammal. In certain such embodiments, the mammal is a human, an equine, a feline, or a canine. In some embodiments, the resistant infection is present on and/or in a wound or as part of an oral disease.

In some embodiments, the biophotonic compositions and methods of the present disclosure are useful in treating resistant infections, for example, by maintaining asepsis. In some embodiments, the biophotonic compositions and methods of the present disclosure are useful in treating resistant infections, for example, by ameliorating any symptom caused by an infectious agent or inhibiting it from spreading. In some embodiments, the biophotonic compositions and methods of the present disclosure are useful in treating resistant infections, for example, by treating or preventing infection. In some embodiments, the biophotonic compositions and methods of the present disclosure are useful in treating resistant infections, for example, by treating or preventing bacterial infection. In some embodiments, the biophotonic compositions and methods of the present disclosure are useful in treating resistant infections, for example, by treating or preventing resistant bacterial infections. In some embodiments, the biophotonic compositions and methods of the present disclosure are useful in treating resistant infection without or with reduced use of antibiotics.

Wounds and Wound Healing

In some embodiments, the biophotonic compositions of the present disclosure are useful in the treatment of wounds of the skin or soft tissues that have a non-resistant or resistant infection, or that are infected by both a non-resistant and a resistant bacteria population, or other pathological agents (e.g. fungi). In certain embodiments, the resistant infection has developed from an infection that was originally a non-resistant infection. In certain such embodiments, the wounds may comprise a non-resistant or resistant infection. In certain such embodiments, the non-resistant or resistant infection is a bacterial infection. In certain such embodiments wherein the resistant infection is a bacterial infection, the bacterial infection is resistant to antibiotics. In certain such embodiments, the wound is present on a patient and the patient is a mammal, such as a human, an equine, a feline, or a canine.

Therefore, it is an objective of the present disclosure to provide a method of providing biophotonic therapy to a wound of the skin or soft tissues that has a non-resistant or resistant infection or a combination of such infections. In certain such embodiments, the wounds comprise a resistant infection. In certain such embodiments, the non-resistant or resistant infection is a bacterial infection. In certain such embodiments wherein the resistant infection is a bacterial infection, the bacterial infection is resistant to antibiotics. In certain such embodiments, the wound is present on a patient and the patient is a mammal, such as a human, an equine, a feline, or a canine.

Wounds that may be treated by the biophotonic compositions and methods of the present disclosure include, for example, injuries to the skin and subcutaneous tissue initiated in different ways (e.g., pressure ulcers from extended bed rest, wounds induced by trauma, wounds induced by conditions such as periodontitis and periodontal disease) and with varying characteristics. In some embodiments, the present disclosure provides biophotonic compositions and methods for treating and/or promoting the healing of, for example, burns, incisions, excisions, lacerations, abrasions, puncture or penetrating wounds, chronic wounds, acute wounds; surgical wounds, contusions; hematomas, crushing injuries, sores and ulcers. Wounds that may be treated by the biophotonic compositions and methods of the present disclosure also include wounds of the skin and soft tissues.

Biophotonic compositions and methods of the present disclosure are useful to treat and/or promote the healing of chronic cutaneous ulcers or wounds, which are wounds that have failed to proceed through an orderly and timely series of events to produce a durable structural, functional, and cosmetic closure.

The present disclosure provides biophotonic compositions and methods for treating and/or promoting healing in Grade I-IV ulcers. In some embodiments, the application provides compositions suitable for use with Grade II ulcers in particular. Ulcers may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

In some embodiments, the present disclosure provides biophotonic compositions and methods for treating and/or promoting healing of a pressure ulcer. Pressure ulcer includes bed or pressure sores, decubitus ulcers and ischial tuberosity ulcers and can cause considerable pain and discomfort to a patient. A pressure ulcer can occur as a result of a prolonged pressure applied to the skin. Thus, pressure can be exerted on the skin of a patient due to the weight or mass of the patient or due to the presence of any type of apparatus on the skin or soft tissue for a prolonged period of time and which may have, periodically, additional weight added to the apparatus, for example a horse saddle or other load-bearing apparatus. A pressure ulcer can develop when blood supply to an area of the skin is obstructed or cut off for more than two or three hours. The affected skin area can turn red, becomes painful and can become necrotic. If untreated, the skin breaks open and can become infected. An ulcer sore is therefore a skin ulcer that occurs in an area of the skin that is under pressure from e.g., lying, sitting, and/or wearing a cast or other apparatus for a prolonged period of time. Pressure ulcer can occur when a patent is bedridden, unconscious, unable to sense pain, or immobile. Pressure ulcer often occur in boney prominences of the body such as the buttocks area (on the sacrum or iliac crest), or on the hips or elbows.

In some embodiments, the present disclosure provides biophotonic compositions and methods for treating and/or promoting healing of traumatic ulcers.

In some embodiments, the present disclosure provides biophotonic compositions and methods for treating and/or promoting healing of acute wounds. An acute wound is an injury to the skin that occurs suddenly rather than over time. Acute wounds can happen anywhere on the body and vary from superficial scratches to deep wounds damaging blood vessels, nerves, muscles or other body parts.

In some embodiments, the present disclosure provides biophotonic compositions and methods for treating and/or promoting healing of chronic wounds. A chronic wound develops when any acute wound fails to heal in the expected time frame for that type of wound, which might be a couple of weeks or up to six weeks in some cases. Failure of any wound to heal can be due to a lack of one or more of the main requirements of healing, including a good supply of blood, oxygen and nutrients, and a clean and infection-free environment.

In some embodiments, the present disclosure provides biophotonic compositions and methods for treating and/or promoting healing of surgical wounds. In certain such embodiments, administration of post-operative antibiotics is not part of the method of treatment. In some embodiments, the present disclosure provides biophotonic compositions and methods for treating and/or promoting healing of surgical dehisced wounds. Wound dehiscence is one of the most common complications of surgical wounds, involving the breaking open of the surgical incision along the suture. When wound dehiscence occurs, the edges starts to separate and the wound reopens instead of healing closed as planned.

Additional types of wounds that can be treated by the biophotonic compositions and methods of the present disclosure include those disclosed by U.S. Pat. Appl. Publ. No. 20090220450, which is incorporated herein by reference.

Any of the types of wounds described herein are susceptible to microbial infection, and in some cases, these infections become resistant infections. In some embodiments, the present disclosure provides biophotonic compositions and methods for treating and/or preventing wounds comprising resistant infections, wherein the wounds are selected from any of the types of wounds described herein.

The present disclosure provides biophotonic compositions and methods for treating any one of the types of wounds described herein, wherein the wound is present on a mammal. In certain such embodiments, the mammal is a human, an equine, a feline, or a canine. Treatment of wounds in mammals such as horses, cats, or dogs can be challenging. Management of the wounds, regardless of size, is frequently laborious and frustrating, as animals tend to lick, chew, or scratch at their wounds. Maintaining asepsis is difficult, and complications, such as infection, can lead to physical pain, emotional distress, and longer healing time.

Wound healing in mammalian tissues is a complicated reparative process. For example, the healing process for skin involves the recruitment of a variety of specialized cells to the site of the wound, extracellular matrix and basement membrane deposition, angiogenesis, selective protease activity and re-epithelialization.

There are three distinct phases in the wound healing process. First, in the inflammatory phase, which typically occurs from the moment a wound occurs until the first two to five days, platelets aggregate to deposit granules, promoting the deposit of fibrin and stimulating the release of growth factors. Leukocytes migrate to the wound site and begin to digest and transport debris away from the wound. During this inflammatory phase, monocytes are also converted to macrophages, which release growth factors for stimulating angiogenesis and the production of fibroblasts.

Second, in the proliferative phase, which typically occurs from two days to three weeks, granulation tissue forms, and epithelialization and contraction begin. Fibroblasts, which are key cell types in this phase, proliferate and synthesize collagen to fill the wound and provide a strong matrix on which epithelial cells grow. As fibroblasts produce collagen, vascularization extends from nearby vessels, resulting in granulation tissue. Granulation tissue typically grows from the base of the wound. Epithelialization involves the migration of epithelial cells from the wound surfaces to seal the wound. Epithelial cells are driven by the need to contact cells of like type and are guided by a network of fibrin strands that function as a grid over which these cells migrate. Contractile cells called myofibroblasts appear in wounds, and aid in wound closure. These cells exhibit collagen synthesis and contractility, and are common in granulating wounds.

Third, in the remodeling phase, the final phase of wound healing which can take place from three weeks up to several years, collagen in the scar undergoes repeated degradation and re-synthesis. During this phase, the tensile strength of the newly formed skin increases.

However, as the rate of wound healing increases, there is often an associated increase in scar formation. Scarring is a consequence of the healing process in most adult animal and human tissues. Scar tissue is not identical to the tissue which it replaces, as it is usually of inferior functional quality. The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion.

In contrast, normal skin consists, in humans, of collagen fibers arranged in a basket-weave pattern, which contributes to both the strength and elasticity of the dermis. Thus, to achieve a smoother wound healing process, an approach is needed that not only stimulates collagen production, but also does so in a way that reduces scar formation.

The biophotonic compositions and methods of the present disclosure promote the wound healing by promoting the formation of substantially uniform epithelialization; promoting collagen synthesis; promoting controlled contraction; and/or by reducing the formation of scar tissue. In some embodiments, the biophotonic compositions and methods of the present disclosure are useful in promoting wound healing by promoting the formation of substantially uniform epithelialization. In some embodiments, the biophotonic compositions and methods of the present disclosure promote collagen synthesis. In some embodiments, the biophotonic compositions and methods of the present disclosure promote controlled contraction. In some embodiments, the biophotonic compositions and methods of the present disclosure promote wound healing, for example, by reducing the formation of scar tissue or by speeding up the wound closure process. In some embodiments, the biophotonic compositions and methods of the present disclosure promote wound healing, for example, by reducing inflammation. In some embodiments, the biophotonic composition can be used following wound closure to optimize scar revision.

In some embodiments, the biophotonic compositions and methods of the present disclosure promote wound healing, for example, by maintaining asepsis. In some embodiments, the biophotonic compositions and methods of the present disclosure promote wound healing, for example, by ameliorating any symptom caused by an infectious agent or inhibiting it from spreading. In some embodiments, the biophotonic compositions and methods of the present disclosure promote wound healing, for example, by treating or preventing infection. In some embodiments, the biophotonic compositions and methods of the present disclosure promote wound healing, for example, by treating or preventing bacterial or fungal infection. In some embodiments, the biophotonic compositions and methods of the present disclosure promote wound healing, for example, by treating or preventing resistant infections or infections that have a population of non-resistant and resistant bacteria or other microorganisms. In some embodiments, the biophotonic compositions and methods of the present disclosure promote wound healing, for example, by treating or preventing resistant bacterial infections. In some embodiments, the biophotonic compositions and methods of the present disclosure promote wound healing, for example, by preventing reinfection of the wound. In some embodiments, the biophotonic compositions and methods of the present disclosure promote wound healing without the use of antibiotics. The biophotonic compositions of the disclosure may be applied at regular intervals such as once a week for one or more weeks, or at an interval deemed appropriate by the physician or veterinarian.

The biophotonic composition may be soaked into a woven or non-woven material or a sponge and applied as a wound dressing. A light source, such as LEDs or waveguides, may be provided within or adjacent the wound dressing or the composition to illuminate the composition. The waveguides can be optical fibers which can transmit light, not only from their ends, but also from their body. In some embodiments, the waveguides are made of polycarbonate or polymethylmethacrylate.

Adjunct therapies which may be topical or systemic such as antibiotic treatment may also be used. Negative pressure assisted wound closure can also be used to assist wound closure and/or to remove the composition.

Oral Diseases

The biophotonic compositions and methods of the present disclosure are useful to treat oral diseases. In certain such embodiments, the oral diseases comprise a non-resistant infection or a resistant infection or a combination of a non-resistant and a resistant infection. In certain embodiments, the resistant infection has developed from a non-resistant infection that was treated by a method not comprising a biophotonic composition of the present description. In certain such embodiments, the non-resistant or the resistant infection, or both, is a bacterial infection. In certain such embodiments wherein the resistant infection is a bacterial infection, the bacterial infection is resistant to antibiotics. In certain such embodiments, the oral disease is present in a patient and the patient is a mammal, such as a human, an equine, a feline, or a canine. The biophotonic compositions of the disclosure may be applied at regular intervals such as once a week, or at an interval deemed appropriate by the physician, dental professional, or veterinarian.

Therefore, it is an objective of the present disclosure to provide a method of providing biophotonic therapy to an oral disease. In certain such embodiments, the oral disease comprises a non-resistant infection or a resistant infection or a combination of a non-resistant and a resistant infection. In certain such embodiments, either or both of the non-resistant and the resistant infections are a bacterial infection. In certain such embodiments wherein the resistant infection is a bacterial infection, the bacterial infection is resistant to antibiotics. In certain such embodiments, the oral disease is present on a patient and the patient is a mammal, such as a human, an equine, a feline, or a canine. The oral disease may be chosen from, but is not limited to, gingivitis, periodontitis, periodontal disease, and oral lesions.

Gingivitis

Gingivitis is a disorder that is defined by the inflammation of the gums, and is characterized as a periodontal disease, which is characterized by the destruction of the gums, tissue, tooth sockets, and ligaments which create the structure that holds the teeth in place. Gingivitis is one of the first stages of serious periodontal disease.

The symptoms of gingivitis include swollen gums, mouth sores, a bright red or purple appearance to the gums, shiny gums, gums that are painless except when touched, and bleeding gums. Often the first signs of gingivitis have no symptoms except for visual symptoms and are likely only to be diagnosed by a dental professional or veterinarian specializing in the treatment of oral diseases in animals.

Periodontal Disease

Periodontal disease (PD) is more prevalent in developing nations and in most cases, a professional cleaning and antibiotics can clear up most cases of periodontal disease in humans. Periodontal diseases are also prevalent in non-human mammals, and as per the situation with human periodontal disease, if left untreated the infection can spread throughout the body and can lead to serious health complications. In many instances, treatment of the periodontal disease in an afflicted non-human mammal entails an extraction of the entire tooth.

PD consists of an infection of the periodontium and can result in serious local consequences (oro nasal fistulas, class 11 perio-endo lesions, pathologic fractures, ocularproblems, osteomyelitis, and increased incidence of oral cancer) and systemic complications (renal, hepatic, pulmonary, and cardiac diseases; osteoporosis, adverse pregnancy effects, and diabetes mellitus). PD has a multifactorial etiology although, at the onset, bacterial plaque plays a role of prime importance. Plaque is a biofilm, which is made up almost entirely of oral bacteria, contained in a matrix composed of salivary glycoproteins and extracellular polysaccharides. Calculus (or tartar) is basically plaque which has secondarily become calcified by the minerals in saliva. In some embodiments, the present disclosure provides biophotonic compositions and methods for treating and/or promoting healing of wounds associated with PD1; gingivitis only without attachment loss; PD2, early periodontitis with <25% of attachment loss; PD3, moderate periodontitis with 25-50% attachment loss; or PD4, advanced periodontitis with >50% attachment loss.

Symptoms of periodontal disease include painful gums, bad breath, a foul taste to the mouth, fever, gums that bleed with only mild amounts of pressure, crater sized canker sores between the teeth and gums, swollen lymph nodes around the head, neck, or jaw, a gray film on the gums, red gums, swollen gums, and pain when eating and swallowing.

Periodontitis

Periodontitis or Pyorrhea alveolaris is the inflammation of the periodontium which comprises tissues supporting the teeth in the oral cavity. Parts included in the periodontium are the gingiva (gum tissue), the alveolar bone which are sockets where teeth are attached, the cementum or outer layer of teeth roots and the periodontal ligaments or PDL composed of connective tissue fibers linking the gingival and cementum to the alveolar bone. The condition is described as the progressive loss of bone around teeth leading to loose teeth or loss of teeth if left unattended. There are different causes for the disease in which bacteria is the most common. Periodontitis is considered as an advanced phase of gum disease since it already involves bone loss in the area. It is the effect of mild gingivitis being left untreated. Due to the presence of bacterial infection, the body can also respond negatively to it leading to further complications. The condition is one of the leading causes of tooth loss among human adults, affecting around 50% of everyone over the age of 30.

Signs and symptoms arise due to the unstable anchoring of teeth as well as the presence of microorganisms. Gums occasionally or frequently bleed or turn red while brushing teeth, using dental floss, biting into food, chewing or touching with fingers. Gums swell or develop pus occasionally as well. The affected individual likely has halitosis or bad breath and, in humans, have a lingering metallic or tinny taste inside the mouth. Teeth, in afflicted humans, seem longer and sharper due to gingival recession which partly may also be caused by hard brushing. If enzymes called collagenases have begun destroying collagen, the person will have deep pockets between the teeth and gums. In some embodiments, biophotonic compositions of the present disclosure are applied to the periodontal pockets of a subject.

During the early stages of periodontal disease, only a few signs and symptoms may be noticeable. Aggressive periodontitis may affect younger individuals and can occur in episodes. Some episodes may present very mild symptoms while others may be very severe. The signs and symptoms especially in the case of chronic periodontitis are usually progressive in nature.

Other Oral Inflammatory Lesions

The present disclosure may be used to treat other types of oral inflammation, including but not limited to oral mucositis, oral ulcers caused by viral, bacterial, fungal or protozoan infections. Included is glossitis, an inflammation or infection of the tongue. It causes the tongue to swell and change color.

Any of the types of oral diseases described herein are susceptible to microbial infection, and in some cases, these infections become resistant infections. In some embodiments, the present disclosure provides biophotonic compositions and methods for treating and/or preventing oral disease comprising a non-resistant or resistant infection or both non-resistant and resistant infections, wherein the oral diseases are selected from any of the types of oral diseases described herein.

In some embodiments, the biophotonic compositions and methods of the present disclosure are useful in treating oral diseases, for example, by maintaining asepsis. In some embodiments, the biophotonic compositions and methods of the present disclosure are useful in treating oral diseases, for example, by ameliorating any symptom caused by an infectious agent or inhibiting it from spreading. In some embodiments, the biophotonic compositions and methods of the present disclosure are useful in treating oral diseases, for example, by treating or preventing infection. In some embodiments, the biophotonic compositions and methods of the present disclosure are useful in treating oral diseases, for example, by treating or preventing bacterial infection. In some embodiments, the biophotonic compositions and methods of the present disclosure are useful in treating oral diseases, for example, by treating or preventing a non-resistant or a resistant infection or a combination of a non-resistant and resistant infection. In some embodiments, the biophotonic compositions and methods of the present disclosure are useful in treating oral diseases, for example, by treating or preventing resistant bacterial infections. In some embodiments, the biophotonic compositions and methods of the present disclosure are useful in treating oral diseases, for example, by preventing reoccurrence of the oral disease or for preventing a non-resistant infection from evolving into a resistant infection. In some embodiments, the biophotonic compositions and methods of the present disclosure are useful in treating oral diseases without or with reduced use of antibiotics.

In some aspects, there is provided a method of treating a skin or soft tissue wound having a non-resistant or a resistant infection, or both categories of infection, comprising: applying a biophotonic composition to a patient in need thereof, wherein the biophotonic composition comprises at least one oxidant and at least one chromophore capable of activating the oxidant; and exposing said biophotonic composition to actinic light for a time sufficient for said chromophore to cause activation of said oxidant. In certain such aspects, the soft tissue wound comprises an oral disease. In certain such aspects, the wound is a skin wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline or a canine. In certain such aspects, the infection is a resistant infection. In certain such aspects, the method is performed once per week for one or more weeks, such as for one week, two weeks, three weeks, four weeks, five weeks, or six weeks. In certain such aspects, the method is performed twice per week for one or more weeks, such as twice per week for one week, two weeks, three weeks, four weeks, five weeks, or six weeks.

In other aspects, the disclosure provides for use of a biophotonic composition for the manufacture of a medicament for treating a patient afflicted with a skin or soft tissue wound having a non-resistant infection or a resistant infection or both categories of infection, wherein said composition comprises: at least one oxidant, and at least one chromophore capable of activating the oxidant; in association with a pharmacologically acceptable carrier. In certain such aspects, the soft tissue wound comprises an oral disease. In certain such aspects, the wound is a skin wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline or a canine. In certain such aspects, the infection is a resistant infection.

In some other aspects, the disclosure provides for use of a biophotonic composition for the treatment of a patient afflicted with a skin or soft tissue wound having a non-resistant or a resistant infection or both categories of infection, wherein said composition comprises: at least one oxidant; and at least one chromophore capable of activating the oxidant; in association with a pharmacologically acceptable carrier. In certain such aspects, the soft tissue wound comprises an oral disease. In certain such aspects, the wound is a skin wound. In certain such aspects, either or both the non-resistant and the resistant infection is a bacterial infection. In certain such aspects, the bacterial infection is resistant to antibiotics. In certain such aspects, the patient is a mammal, such as a human, an equine, a feline or a canine. In certain such aspects, the infection is a resistant infection.

Combination Therapies

Any of the biophotonic compositions, methods, or uses of this disclosure may be useful in combination with other therapeutics.

In some embodiments, the phrase "combination therapy" embraces the administration of any of the compositions described herein, and an additional therapeutic agent, or mixtures of them, as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. The therapeutic agents can be administered by the same route or by different routes. For example, a first therapeutic agent of the combination selected may be administered by intravenous injection or orally while the biophotonic composition of the disclosure is administered topically. Alternatively, for example, all therapeutic agents may be administered topically. The sequence in which the therapeutic agents are administered is not narrowly critical. "Combination therapy" also embraces the administration of the compositions as described herein in further combination with other biologically active ingredients (such as, but not limited to, a second and different therapeutic agent) and/or non-drug therapies (such as, but not limited to, surgery or radiation).

In some embodiments, the therapeutic agents administered in combination therapy simultaneously, separately, or sequentially with any of the compounds and compositions of this disclosure, or mixtures thereof, can comprise, but are not limited to: a non-steroidal anti-inflammatory drug (NSAID), an anti-inflammatory agent, a corticosteroid, an anti-allergic agent, a steroid drug, one or more of the antimicrobial agents described above, one or more collagens and/or agents that promote collagen synthesis described above, or mixtures thereof.

In some embodiments, any of the compositions described herein can allow the combination therapeutic agents and/or compositions described herein or mixtures thereof to be administered at a low dose, that is, at a dose lower than has been conventionally used in clinical situations.

Alternatively, the methods and combinations of this disclosure maximize the therapeutic effect at higher doses.

In some embodiments, when administered as a combination, the therapeutic agents can be formulated as separate compositions which are given at the same time or different times, or the therapeutic agents can be given as a single composition.

Kits

The present disclosure also provides kits for preparing and/or applying any of the compositions of the present disclosure for the treatment of a skin or soft tissue wound having a resistant or non-resistant infection. The kit may include a biophotonic composition (e.g., a topical biophotonic composition), as described herein, and may also include an apparatus for applying or removing the composition, and instructions of use for the composition and/or a light source. In some embodiments, the biophotonic composition comprises at least one oxidant and at least one chromophore capable of activating the oxidant.

In some embodiments, the kit includes more than one composition, for example, a first and a second composition. The first composition may include at least one chromophore capable of activating the oxidant and the second composition may include at least one oxidant. In certain such embodiments, the oxidant is chosen from hydrogen peroxide, carbamide peroxide and benzoyl peroxide. In certain such embodiments, the first and/or second composition further comprises one or more gelling agents.

In some embodiments, the first composition may comprise at least one chromophore capable of activating the oxidant in a liquid or as a powder, and the second composition may comprise at least one oxidant. In certain such embodiments, the oxidant is chosen from hydrogen peroxide, carbamide peroxide and benzoyl peroxide. In certain such embodiments, the first and/or second composition further comprises one or more gelling agents.

In some embodiments, the kit includes containers comprising the compositions of the present disclosure. In some embodiments, the kit includes a first container comprising the at least one chromophore capable of activating the oxidant, and a second container comprising at least one oxidant. In certain such embodiments, the oxidant is chosen from hydrogen peroxide, carbamide peroxide and benzoyl peroxide. In certain such embodiments, the first and/or second composition further comprises one or more gelling agents.

The containers may be light impermeable, air-tight and/or leak resistant. Exemplary containers include, but are not limited to, syringes, vials, or pouches. The first and second compositions may be included within the same container but separated from one another until a user mixes the compositions. In some embodiments, the container may be a dual-chamber syringe where the contents of the chambers mix on expulsion of the compositions from the chambers. In some embodiments, the pouch may include two chambers separated by a frangible membrane. In some embodiments, one component may be contained in a syringe and injectable into a container comprising the second component.

The biophotonic composition may also be provided in a container comprising one or more chambers for holding one or more components of the biophotonic composition, and an outlet in communication with the one or more chambers for discharging the biophotonic composition from the container.

In some embodiments, the kit comprises a systemic or topical drug for augmenting the treatment of the composition. For example, in certain such embodiments, the kit may include a systemic or topical antibiotic or hormone treatment for a non-resistant or resistant infection or both.

Written instructions on how to use the biophotonic composition in accordance with the present disclosure may be included in the kit, or may be included on or associated with the containers comprising the compositions of the present disclosure.

In some embodiments, the kit may comprise a further component which is a dressing. The dressing may be a porous or semi-porous structure for receiving the biophotonic composition. The dressing may comprise woven or non-woven fibrous materials.

In some embodiments of the kit, the kit may further comprise a light source such as a portable light with a wavelength appropriate to activate the chromophore in the biophotonic composition. The portable light may be battery operated or re-chargeable.

In some embodiments, the kit may further comprise one or more waveguides.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present disclosure. They are not intended to limit or define the entire scope of this disclosure.

It should be appreciated that the disclosure is not limited to the particular embodiments described and illustrated herein but includes all modifications and variations falling within the scope of the disclosure as defined in the appended embodiments.

1. Use of Biophotonic Compositions for the Treatment of Wounds (e.g., Surgical or Traumatic Wounds) in Canines and Felines The biophotonic compositions and methods of the disclosure were tested to analyze significant acceleration of wound healing in canines and/or felines for the areas treated with biophotonic therapy compared to those treated in the classical/conventional way.

The study was conducted on three groups of patients (dogs or cats) each composed of at least 50 patients:

The first group consisted of patients that have simple surgical wounds from orthopedic (joint) or neurological surgeries. From the first day after operation (T0) and then every other day, 50% of the length of the surgical wound was treated with biophotonic therapy using a biophotonic composition comprising a carrier gel comprising peroxide (in the form of urea peroxide) and a chromophore-containing gel (final chromophore concentration of 0.01% w/w), while 50% was treated with sterile saline. In cases where patients exhibited two surgical wounds (common in joint diseases often congenital and bilateral), one was treated with the biophotonic composition and the other treated daily with sterile saline. This procedure was conducted for 14 days.

The second group consisted of patients suffering from:
Delayed healing of surgical dehiscent and ulcerated wounds,
Protracted decubital ulcers,
Traumatic ulcers, and
Burns.

The subjects included in this study were treated with the biophotonic therapy, for 5 minutes every 3 days until healing occurred. Every three days, the treatment area was cleaned with sterile isotonic saline and then treated with the biophotonic therapy. After treatment, the wound was covered with a three-layer bandage. The therapy was suspended after complete healing of the wound.

The third group, namely the control group of group two, consisted of patients that, as in the second group, were affected by:
Delayed healing of surgical dehiscent and ulcerated wounds,
Protracted decubital ulcers,
Traumatic ulcers, and
Burns.

They were treated according to a traditional technique that consists of cleaning the injured area with sterile isotonic saline, followed by application of sterile paraffin-impregnated gauzes and covering with a three-layer bandage. This procedure was applied every 3 days until wound healing was complete.

All wounds were clinically evaluated at the beginning of treatment (T0) and then monitored during the treatment.

The lesion area, for each treatment was calculated using a planimetric dedicated software. In each phase of treatment (every other day for group one and every three days for groups two and three) the lesion was photographed and its area was calculated to objectively monitor the progression of healing.

To track the possible presence of infectious complications (bacterial), samples were collected by swabbing at T0, and then, subsequently every 3 days for the duration of the treatment, for bacteriological culture.

All patients in the study were hospitalized and underwent clinical, laboratory and instrumental exams to verify general good health. Any patients with moderate or severe systemic diseases of any nature were excluded from the study.

An Elizabethan collar was applied to all patients for the duration of the study.

Data from the study are summarized in the table 1 below:

TABLE 1

Figure 4:
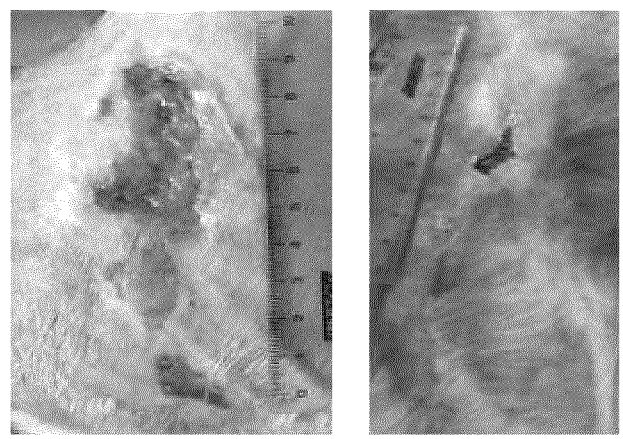
FIG. 4 presents photographs of healing of a traumatic wound for a canine patient (patient 6). The patient was treated five times with a biophotonic composition comprising 6% by weight urea peroxide. During each treatment, the biophotonic composition was exposed to actinic light for five minutes.
Figure 5:
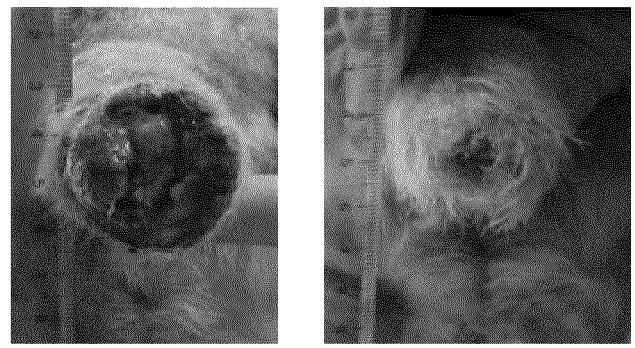
FIG. 5 presents photographs of healing of a tail surgery wound dehiscence for a canine patient (patient 7). The patient was treated seven times with a biophotonic composition comprising 6% by weight urea peroxide. During each treatment, the biophotonic composition was exposed to actinic light for five minutes.
Figure 6:
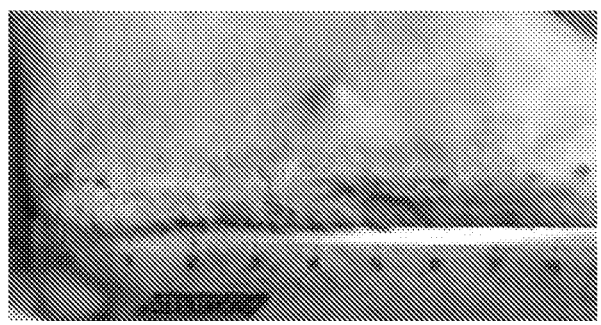
FIG. 6 presents photographs of healing of a surgical wound for a canine patient (patient 11). The patient was treated four times with a biophotonic composition comprising 3% by weight urea peroxide. During each treatment, the biophotonic composition was exposed to actinic light for two minutes. The first treatment with the biophotonic composition was performed during surgery.
Figure 6:
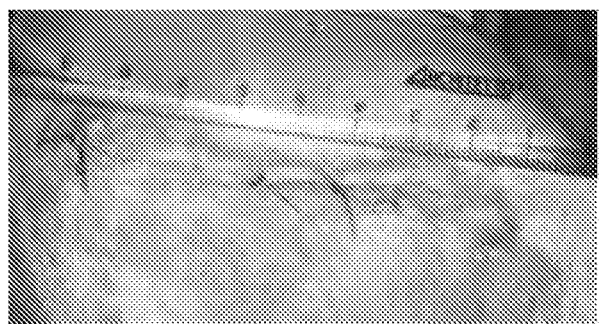
Figure 6:
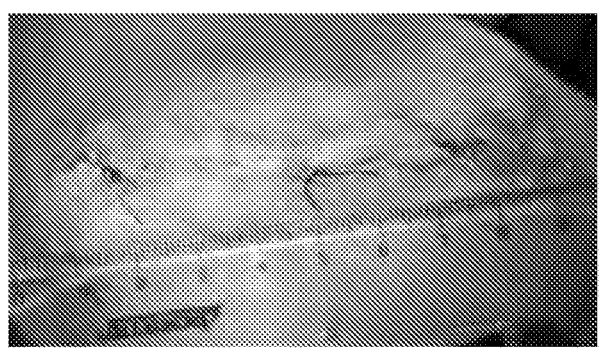
Figure 6:
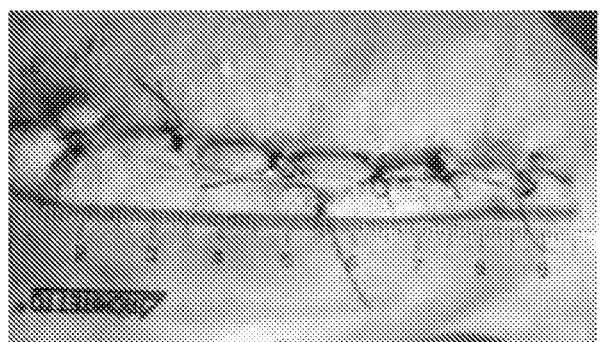
Figure 7:
FIG. 7 presents photographs of healing of a surgical wound for a canine patient (patient 17). The patient was treated three times with a biophotonic composition comprising 3% by weight urea peroxide. During each treatment, the biophotonic composition was exposed to actinic light for two minutes. The first treatment with the biophotonic composition was performed during surgery.
Figure 7:
Figure 7:
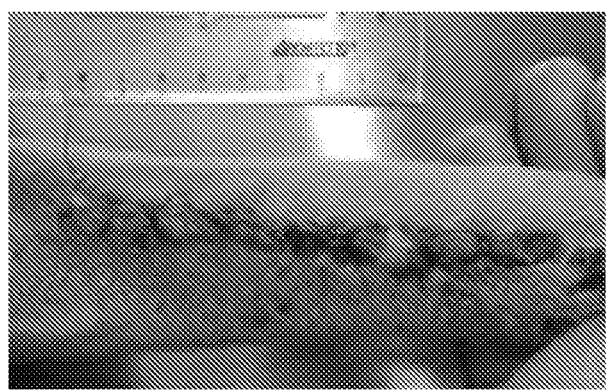
Figure 8A:
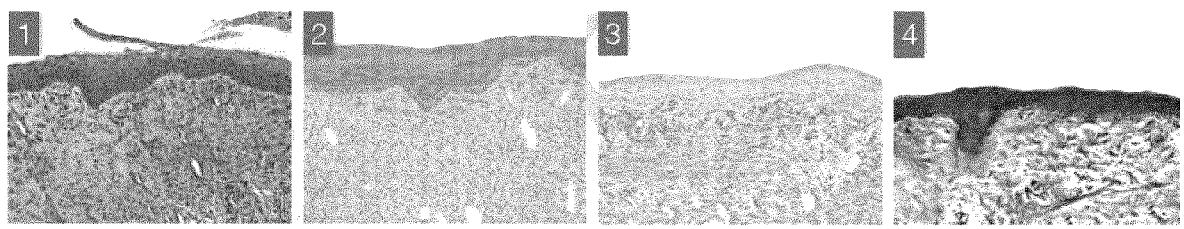
FIGS. 8A and 8B present tissue analysis of healing of a surgical wound for a canine patient (patient 17).
Figure 8B:
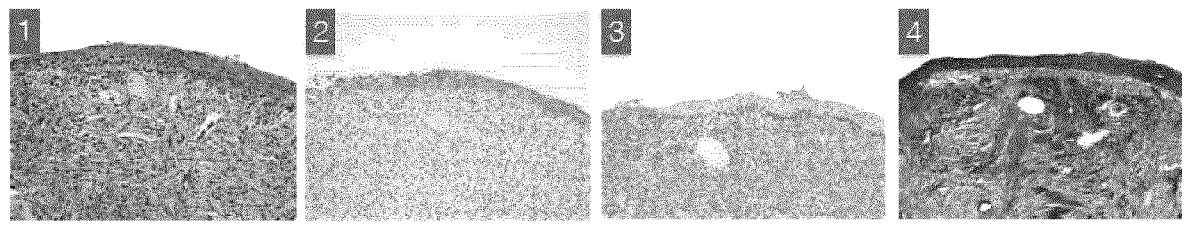
Figure 9A:
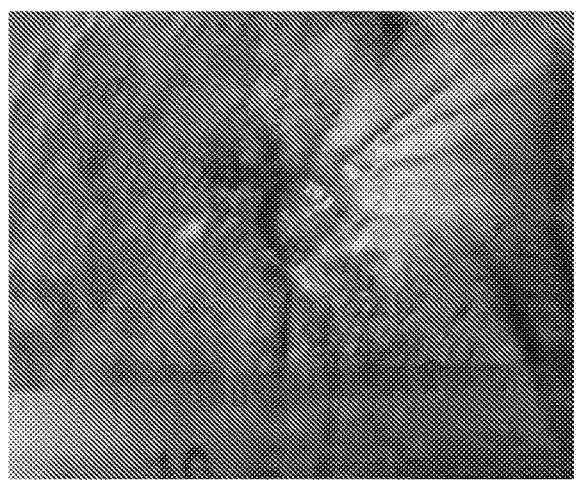
FIGS. 9A-9G presents photographs of biophotonic therapy of a dehisced wound for a canine patent (patient 12). The patient was treated five times with a biophotonic composition comprising 6% by weight urea peroxide. During each treatment, the biophotonic composition was exposed to actinic light for 3.3 minutes.
Figure 9A:
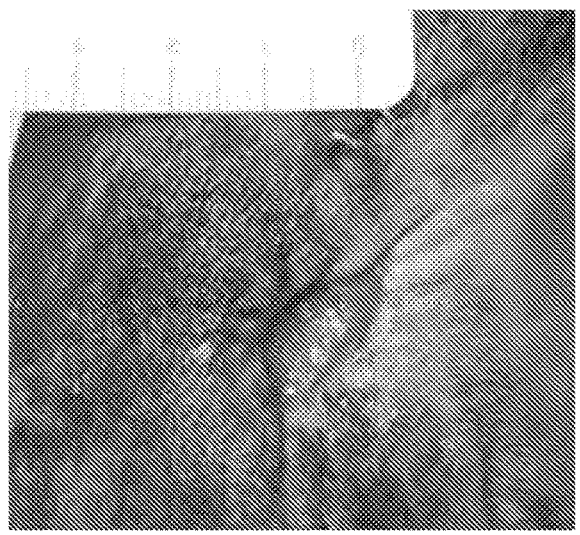
Figure 9A:
Figure 9B:
Figure 9B:
Figure 9B:
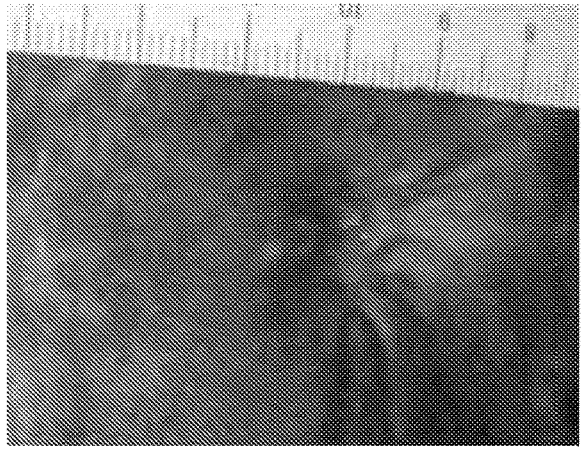
Figure 9C:
Figure 9C:
Figure 9C:
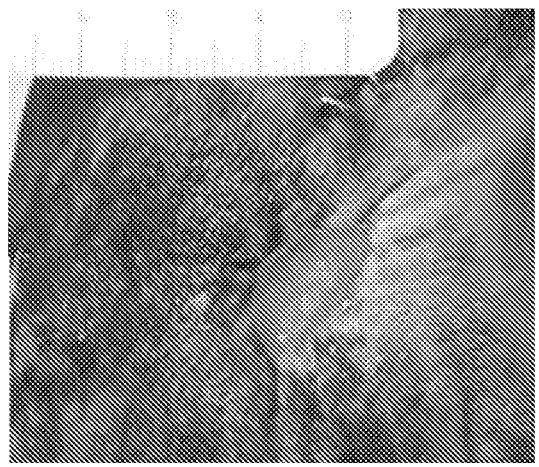
Figure 9C:
Figure 9C:
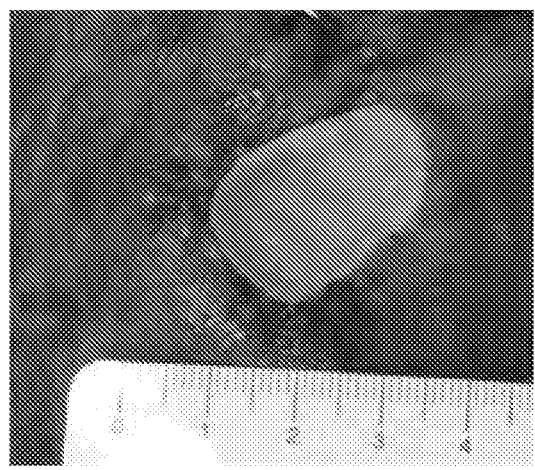
Figure 9C:
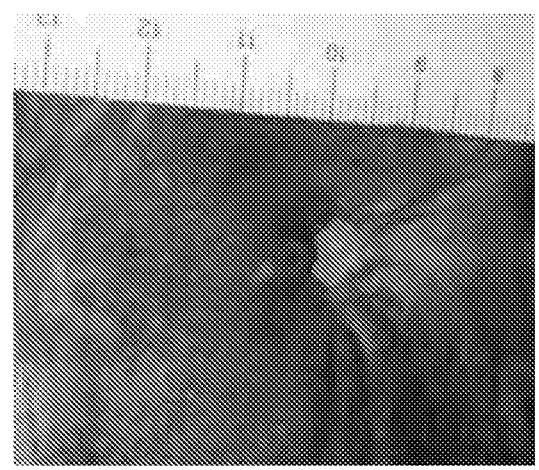
Figure 9D:
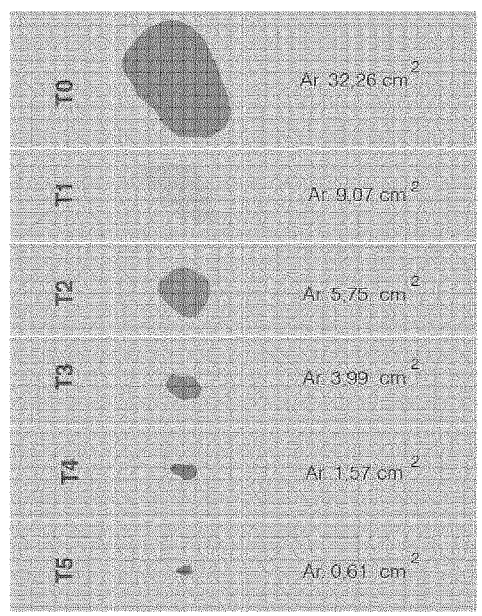
Figure 9E:
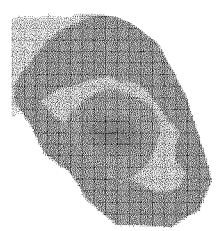
Figure 9F:
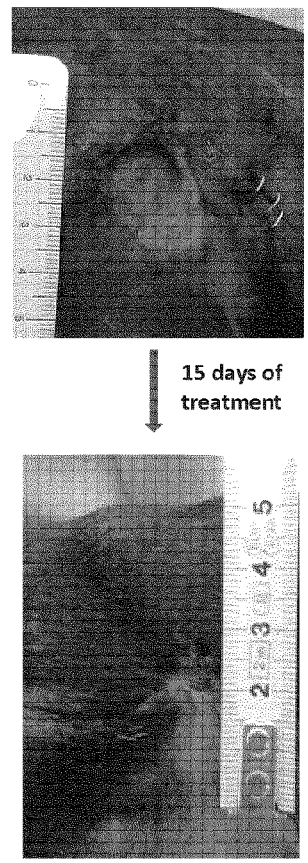
Figure 9G:
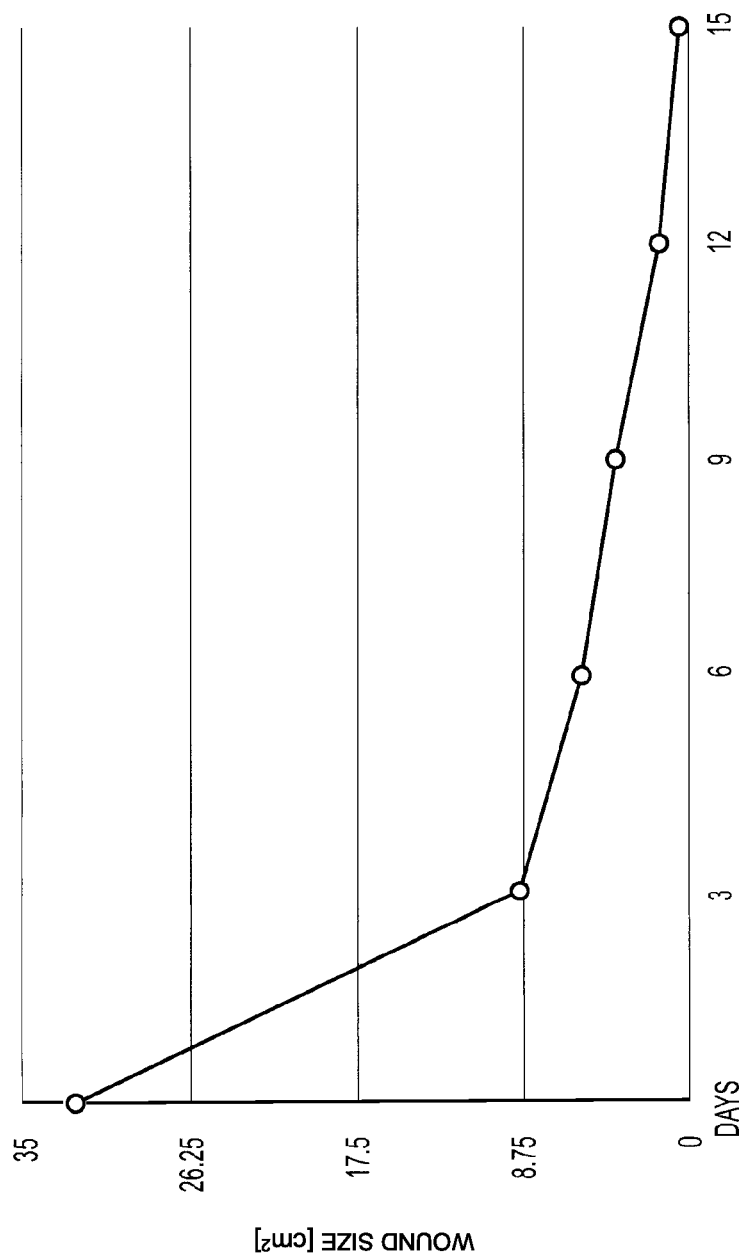
Figure 10:
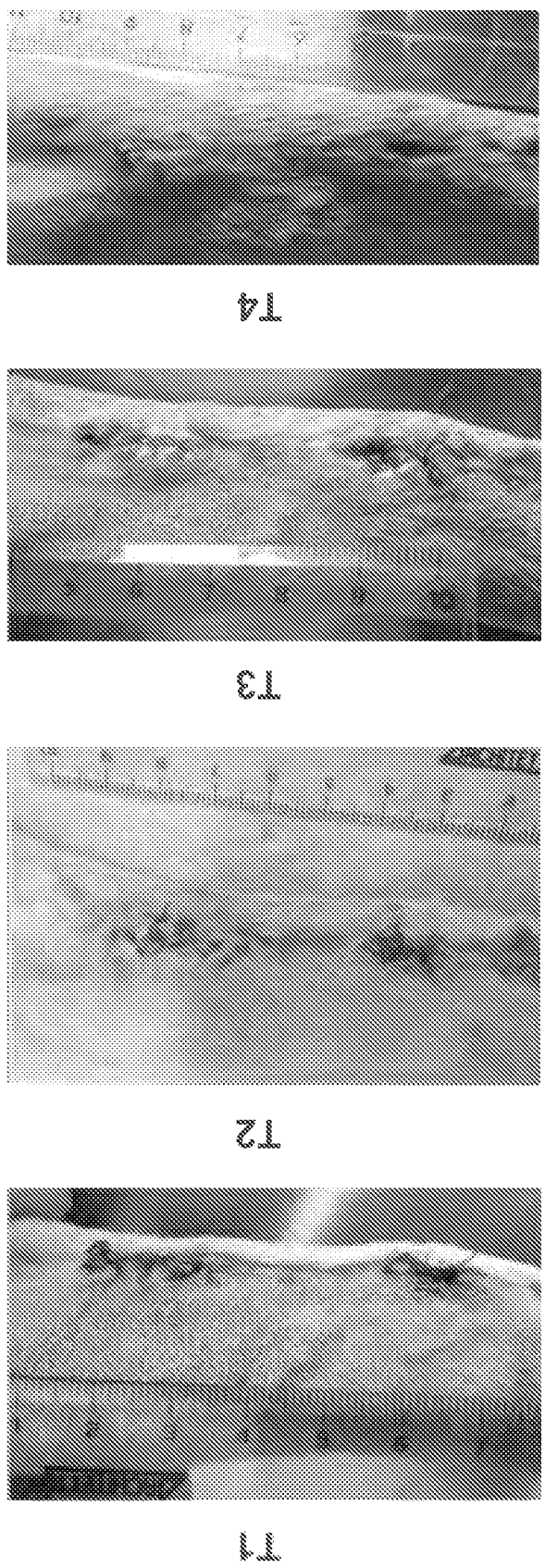
FIG. 10 presents photographs of healing of a surgical wound for a canine patient (patient 10). The patient was treated five times with a biophotonic composition comprising 3% by weight urea peroxide. During each treatment, the biophotonic composition was exposed to actinic light for two minutes. The first treatment with the biophotonic composition was performed during surgery.
Figure 11A:
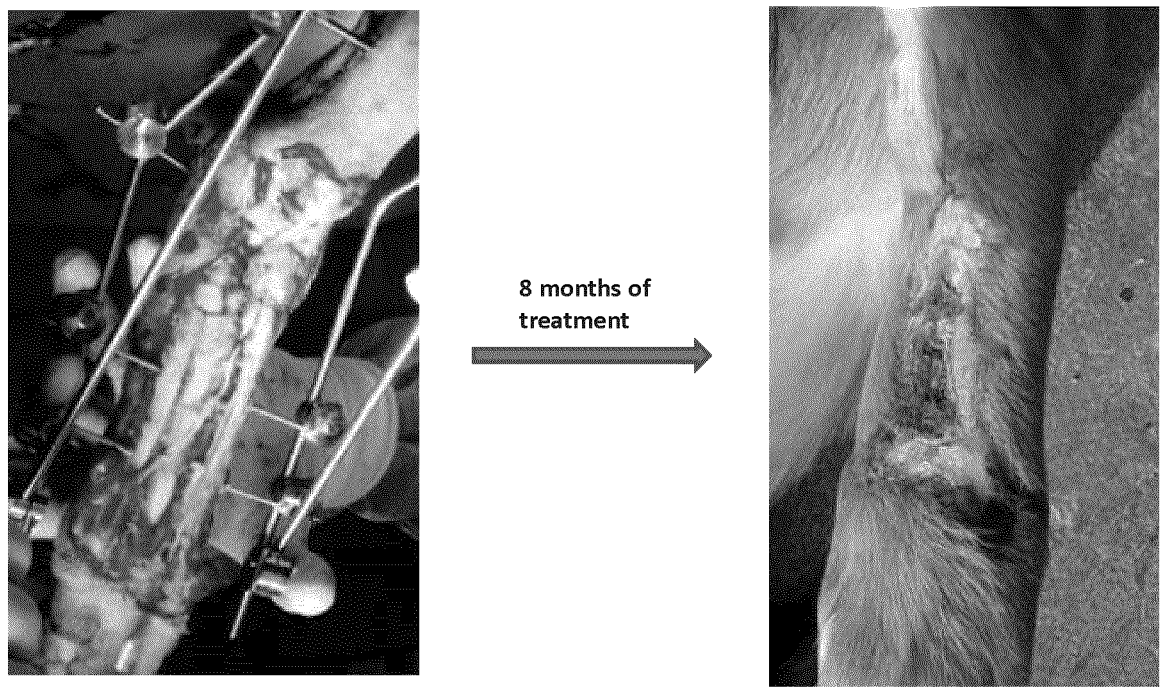
FIGS. 11A and 11B present photographs of healing of a traumatic injury (shearing injury) in a control canine patient (FIG. 11A) and patient 16 (FIG. 11B). The control patient was given eight months of conventional treatment, whereas the patient 16 was treated seven times over 30 days with a biophotonic composition comprising 6% by weight urea peroxide. During each treatment, the biophotonic composition was exposed to actinic light for 3.3 minutes. The first treatment with the biophotonic composition was performed during surgery.
Figure 11B:
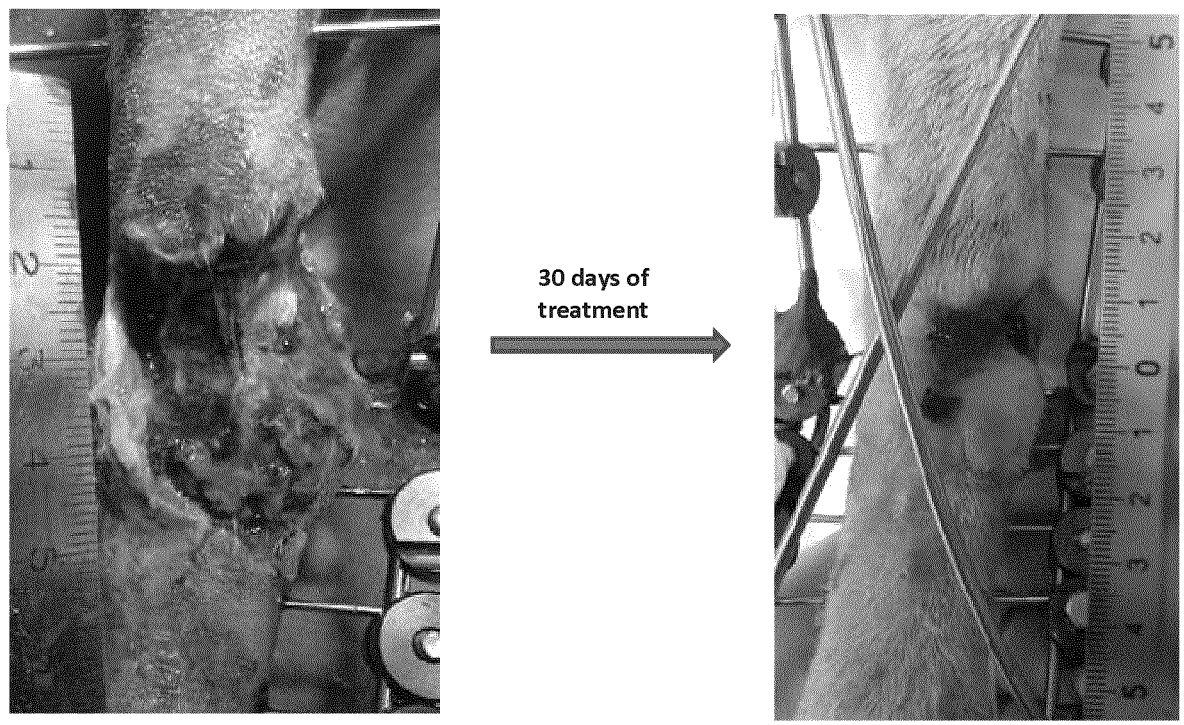
Figure 22:
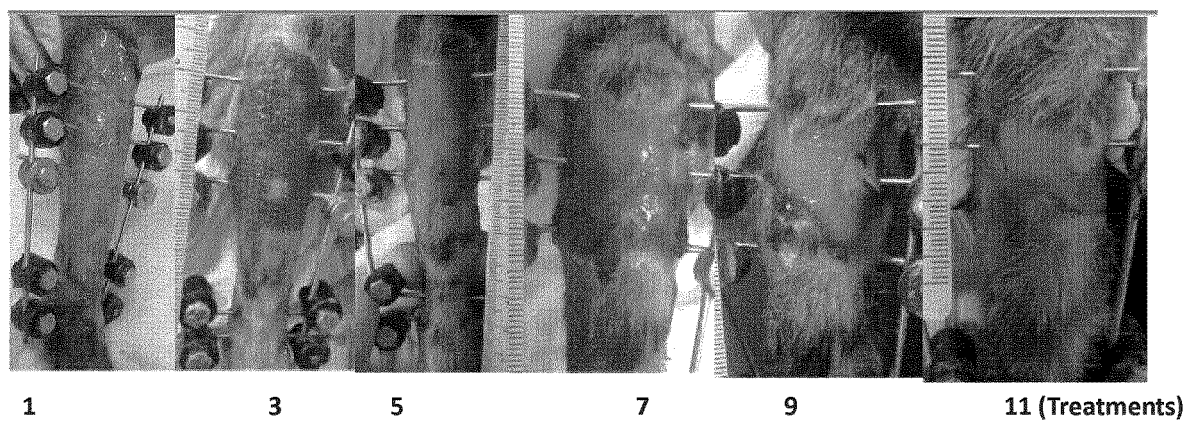
FIG. 22 present photographs of healing of a traumatic wound for a cat patient (case 29) treated with the biophotonic composition of this disclosure.

| Patient Number | Wound Type | No. of Treatments | Intra-surgical Application[a] | No. of Treated Layers[b] | % UP[c] | Exposure Time/ Treatment (minutes)[d] | FIG. with data |
|---|---|---|---|---|---|---|---|
| 1 | Surgical | 4 | No | 1 (s) | 12 | 2 | N/A |
| 2 | Surgical | 6 | Yes | 2 (s, sb) | 6 | Not reported | N/A |
| 3 | Surgical | 4 | Yes | 2 (s, sb) | 6 | 5 | N/A |
| 4 | Surgical | 4 | Yes | 3 (s, sb, m) | 6 | 5 | N/A |
| 5 | Surgical | 3 | Yes | 2 (s, sb) | 6 | Not reported | N/A |
| 6 | Traumatic | 5 | No | 3 (s, sb, m) | 6 | 5 | FIG. 4 |
| 7 | Dehisced | 7 | No | 3 (s, sb, m) | 6 | 5 | FIG. 5 |
| 8 | Dehisced | 6 | No | 2 (s, sb) | 6 | Not reported | N/A |
| 9 | Ulcer | 6 | No | 3 (s, sb, m) | 6 | Not reported | N/A |
| 10 | Surgical | 5 | Yes | 3 (s, sb, m) | 3-6 | 2 | FIG. 10 |
| 11 | Surgical | 4 | Yes | 3 (s, sb, m) | 3-6 | 2 | FIG. 6 |
| 12 | Dehisced | 5 | No | 3 (s, sb, m) | 6 | 3.3 | FIGS. 9A-9G |
| 13 | Surgical | 4 | Yes | 3 (s, sb, m) | 3 | Not reported | N/A |
| 14 | Dehisced | 9 | No | 3 (s, sb, m) | 6 | Not reported | N/A |
| 15 | Dehisced | 11 | No | 4 (s, sb, m, b) | 3 | Not reported | N/A |
| 16 | Traumatic | 7 | Yes | 4 (s, sb, m, b) | 6 | 3.3 | FIG. 11B[e] |
| 17 | Surgical | 3 | Yes | 3 (s, sb, m) | 3 | 2 | FIGS. 7, 8A-8B |
| 18 | Traumatic | 3 | No | 2 (s, sb) | 6 | Not reported | N/A |
| 19 | caustic | 5 | No | 2 (s, sb) | 6 | Not reported | N/A |
| 20 | Insect bite | 11 | No | 3 (s, sb, b) | 6 | Not reported | N/A |
| 21 | Surgical | 3 | Yes | 3 (s, sb, m) | 3 | Not reported | N/A |
| 22 | Traumatic | 3 | No | 4 (s, sb, m, b) | 6 | Not reported | N/A |
| 23 | Flemmone (Phlegmon) | 28 | No | 3 (s, sb, m) | 6 | Not reported | N/A |
| 24 | Flemmone (Phlegmon) | 6 | No | 3 (s, sb, m) | 6 | Not reported | N/A |
| 25 | Traumatic | 8 | No | 3 (s, sb, m) | 6 | 2 | N/A |
| 26 | Flemmone (Phlegmon) | 3 | No | 3 (s, sb, m) | 6 | Not reported | N/A |
| 27 | Traumatic | 4 | No | 3 (s, sb, m) | 6 | Not reported | N/A |
| 28 | Traumatic | 19 | Yes | 5 (s, sb, m, b, t) | 6 | Not reported | N/A |
| 29 | Infection Skin | 11 | No | 2 (s, sb) | 6 | 2 | FIG. 22 |
| 30 | Traumatic | 6 | Yes | 3 (s, sb, m) | 6 | Not reported | N/A |
| 31 | Traumatic | 7 | No | 5 (s, sb, m, b, t) | 6 | Not reported | N/A |
| 32 | Traumatic | 2 | No | 2 (s, sb) | 6 | Not reported | N/A |
| 33 | Traumatic | 2 | No | 2 (s, sb) | 6 | Not reported | N/A |

[a] Intra-surgical application refers to whether or not the first treatment with the biophotonic composition was applied during surgery.
[b] The treated wound layers are as follows: s = surface, sb = sub-surface, m = middle; and b = bone.
[c] % UP is the % of urea peroxide by weight of the total composition.
[d] Exposure time was the time the biophotonic composition on the wound was exposed to actinic (e.g., blue) light.
[e] FIG. 11A shows a control subject with a similar injury as patient 16, but the control subject was not treated with biophotonic therapy.

Tissue analysis of healing of a surgical wound for a canine patient (patient 17) is shown in FIGS. 8A and 8B. FIG. 8A shows tissues (surface, subsurface, and middle) which were treated three times with a biophotonic composition comprising 3% by weight urea peroxide. During each treatment, the biophotonic composition was exposed to blue light for two minutes. The first treatment with the biophotonic composition was performed during surgery. FIG. 8B shows tissues not treated with biophotonic therapy (a control sample).

Comparing the time course of healing as presented in panels 1 to 4 of FIG. 8A versus those of FIG. 8B, it is evident that the wound that received the application of the biophotonic composition treatment healed, to complete closure, at a faster rate than the wound that did not receive the application of the biophotonic composition treatment. Furthermore, as can be seen in panel 4 of FIG. 8A versus FIG. 8B, both the epithelial and underlying cell layers in the treated wound appear organized in a fashion that would be close to that of unwounded canine skin tissue, while the wound that did not receive the biophotonic composition treatment had a thinner epidermal layer and the underlying cell layers had a pronounced degree of disorganization even though the wound had closed.

Tests were also conducted to analyze healing of a traumatic injury (shearing injury) in a control canine patient (FIG. 11A) and patient 16 (FIG. 11B). The tissues treated were surface, sub-surface, middle, and bone. The control patient was given eight months of conventional treatment, whereas the patient 16 was treated seven times over 30 days with a biophotonic composition comprising 6% by weight urea peroxide. During each treatment, the biophotonic composition was exposed to blue light for 3.3 minutes. The first treatment with the biophotonic composition was performed during surgery. Without wishing to be bound by theory, biophotonic therapy appeared to shorten the healing time required for the shearing injury.

The studies also examined whether antibiotics were needed in the treatment of the wounds. Patient 12 received treatment of a dehisced wound with biophotonic therapy and no antibiotic treatment (FIGS. 9A-9G). Patient 10 (FIG. 10) received treatment of a surgical wound with biophotonic therapy and no post-operative antibiotic treatment (only pre-operative antibiotic treatment). The tissues treated in Patients 10 and 12 surface, sub-surface, and middle. In patient 16 (FIG. 11B), antibiotic resistant *Pseudomonas* was observed at T0, but after treatment with biophotonic therapy in the absence of antibiotics, a reduced number of colony forming units (CFUs) was observed during bacteriological assessment. Without wishing to be bound by theory, the data illustrate that the compositions, methods, and uses disclosed herein can reduce the microbial load of wounds and are useful in maintaining asepsis during surgeries. Additionally, the compositions, methods, and uses of the disclosure are useful for treating wounds without the use of antibiotics or antimicrobial agents and are useful in the treatment of resistant infections, such as antibiotic resistant infections.

2. Use of Biophotonic Compositions for the Treatment of Wounds in Equines

Natural reactions of horses to danger predispose them to traumatic injuries which can be further complicated by additional trauma, tissue loss, or infection. For horses, injuries are often localized on lower limbs, such as the distal legs, where soft tissue and circulation are poor and joint movement make management and healing difficult. Injury sites on a horse may also occur in other parts of the horse, for example the barrel or the shoulder of the horse as examples. The desirable treatment for horse wounds (traumatic, infective, or surgical) should be cost effective, non-invasive, restorative of function, and also providing satisfactory cosmetic results. Classical wound management in equines includes surgical debridement and lavage, coupled with topical medication and wound dressings. This study evaluated the safety and effect of biophotonic therapy comprising application of a biophotonic composition, as described above, however, comprising 6% urea peroxide (UP), on equine wound healing.

All patients (horses or donkeys) were hospitalized for the duration of the study in the facilities of Veterinary Teaching Hospital, School of Biosciences and Veterinary Medicine, Veterinary Medicine Department, Camerino University.

Horses were divided in two groups named A and B. Group A consisted of horses with surgical wounds (resulting from any surgery) and Group B consisted of horses with naturally occurring wounds, ulcers and sores.

The in vivo efficacy was assessed by evaluating hypersensitivity reactions and swelling after the application of biophotonic therapy. The frequency of application in each group depended on the severity of the wound, but, when possible, it followed the following scheme: weekly, twice a week, or three times a week. The treatment was prolonged for one week after the resolution of the disease. Different protocols were compared for side effects or differences in effectiveness.

Various wound-healing parameters (granulation tissue, crust formation, scar formation, grade of contamination) were visually evaluated daily, and the time points of tissue/wound appearance were documented until no more progress could be noticed for at least 3 weeks. Images of the wound area were obtained using a digital camera, and the dimensions of the wound area and/or length were measured using image analysis software.

Sampling of tissue for histological (when necessary), cytological and microbiological evaluation are performed before, during (at least two times) and after the end of the therapy. A monthly follow-up is performed until six months after the end of the therapy.

Data were analyzed by the Student t-test for group comparisons of normally distributed variables, and $p<0.05$ is considered significant.

Figure 12A:
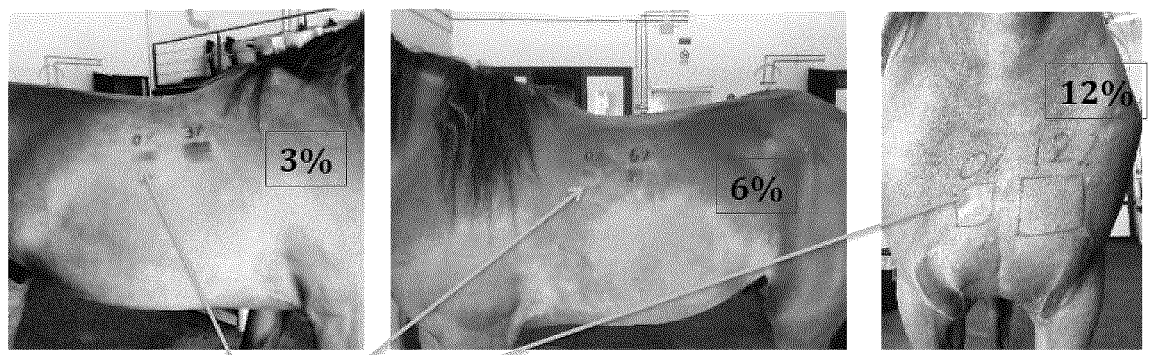
FIGS. 12A and 12B present photographs of a tolerability study for the biophotonic compositions on a six year old healthy gelding Trotter horse.
Figure 12B:
Figure 12B:

The results of tolerability study for the biophotonic compositions on a six year old healthy gelding Trotter horse are shown in FIGS. 12A and 12B and in the table below. As shown in FIG. 12A, three zones of treatment where selected, the left flank, the right flank, and the breast. In each zone, two rectangular areas of different sizes, one small and one large, were clipped. On all small rectangular areas, the chromophore gel with 0% urea peroxide (UP) was applied. On the large rectangular area of the right flank, a 3% UP chromophore gel was applied. On the large rectangular area of the left flank, a 6% UP chromophore gel was applied. On the large rectangular area of the breast, a 12% UP chromophore gel was applied. FIG. 12B shows treatment of the zones with blue light. The areas were treated at a distance of 5 cm with an exposure time of five minutes. Each area was treated two times per week for a total of four weeks (eight treatments per area in total). As shown in the table 2 below, no relevant changes were observed during the course of treatment and there were no negative effects. There were no significant variations in the appearance of the patient's skin or on skin thickness. The data indicated the treatment was well-tolerated at each of the UP concentrations.

TABLE 2

Schedule and results of different activities
SCHEDULE AND RESULTS OF DIFFERENT ACTIVITIES

| | | Time of tolerability study | | | | | | | | | | | | | | |
|---|---|---|---|---|---|---|---|---|---|---|---|---|---|---|---|---|
| | | T0 | | T1 | | T2 | | T3 | | T4 | | T5 | | T6 | | T7 |
| | Action | B | A | B | A | B | A | B | A | B | A | B | A | B | A | B | A |
| Right flank | Clinical [inspection] | nr | nr | nr | nr | nr | nr | nr | nr | nr | nr | nr | nr | nr | nr | nr | nr |
| | Skin thickness [cm] | 0.73 | 0.74 | 0.73 | 0.73 | 0.73 | 0.74 | 0.74 | 0.73 | 0.74 | 0.74 | 0.73 | 0.73 | 0.73 | 0.73 | 0.73 | 0.73 |
| Left flank | Clinical [inspection] | nr | nr | nr | nr | nr | nr | nr | nr | nr | nr | nr | nr | nr | nr | nr | nr |
| | Skin thickness [cm] | 0.73 | 0.73 | 0.73 | 0.73 | 0.73 | 0.73 | 0.74 | 0.74 | 0.74 | 0.72 | 0.72 | 0.73 | 0.73 | 0.72 | 0.73 | 0.73 |
| Breast | Clinical [inspection] | nr | nr | nr | nr | nr | nr | nr | nr | nr | nr | nr | nr | nr | nr | nr | nr |
| | Skin thickness [cm] | 0.73 | 0.73 | 0.73 | 0.73 | 0.74 | 0.74 | 0.72 | 0.74 | 0.72 | 0.73 | 0.73 | 0.73 | 0.74 | 0.73 | 0.73 | 0.73 |
| | Pictures | X | X | | X | | | X | | | | X | | | | | X |

LEGEND:
NR = NOTHING RELEVANT
B = BEFORE
A = AFTER

Figure 13A:
FIGS. 13A-13D present photographs of treatment of a 12 year old female, mixed breed horse with post-traumatic subcutaneous collection of purulent material.
Figure 13B:
Figure 13B:
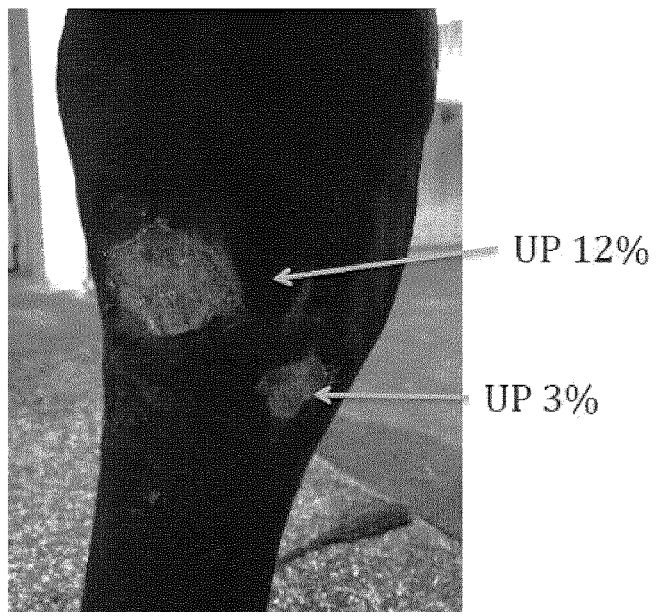
Figure 13C:
Figure 13D:
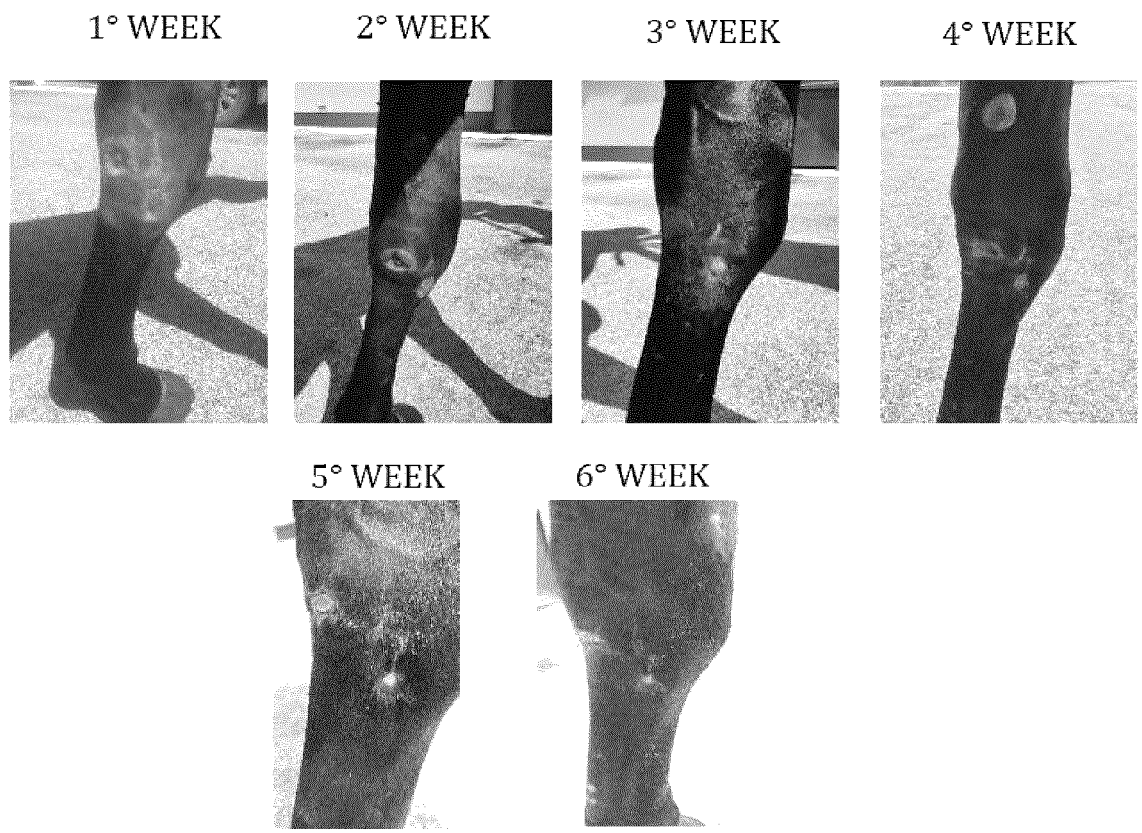

As shown in FIGS. 13A-13D, a 12 year old female, mixed breed horse with post-traumatic subcutaneous collection of purulent material was treated with biophotonic therapy. FIG. 13A illustrates swelling to the left carpal region and two wounds draining purulent material. It also illustrates a fistula located on the palmar surface of the region. FIG. 13B illustrates treatment of the large wound with a biophotonic composition comprising 12% UP and treatment of the small wound with a biophotonic composition comprising 3% UP. FIG. 13C illustrates treatment of the wounds with blue light applied at a distance of 5 cm for five minutes. FIG. 13D illustrates treatment of the wounds over the course of six weeks. The wounds were treated once a week over the course of the six weeks, and healing time appeared to be reduced compared to that observed with conventional treatment.

Figure 14A:
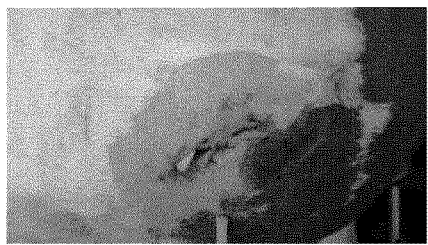
FIGS. 14A-14E present photographs of treatment of a 14 year old female, mixed breed horse with an old wound on the lateral surface of the chest.
Figure 14A:
Figure 14B:
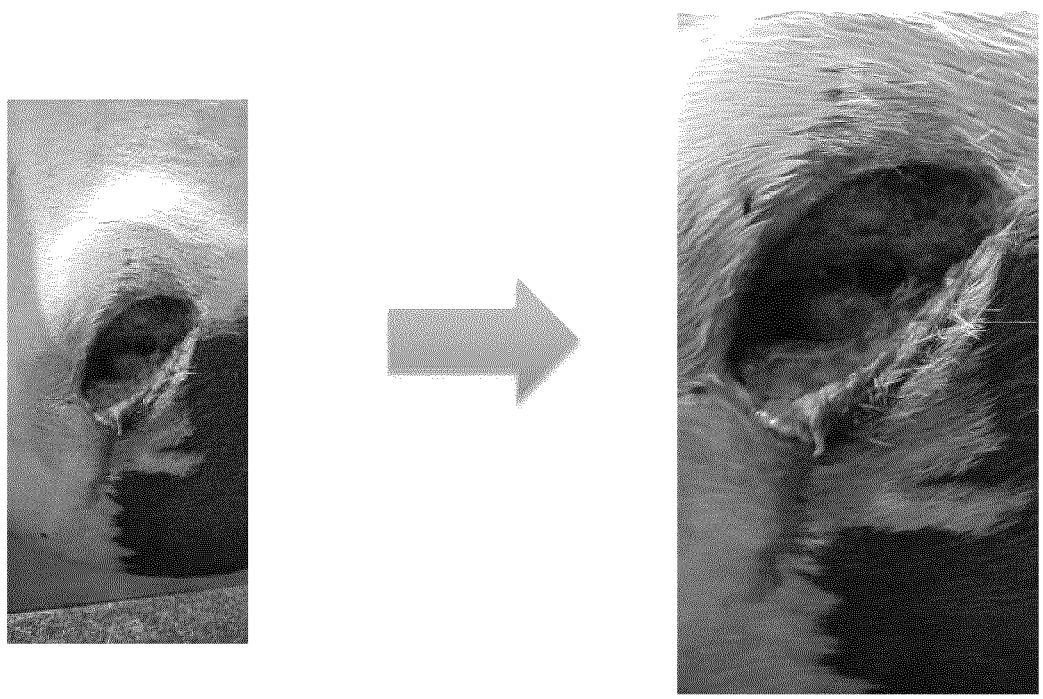
Figure 14C:
Figure 14C:
Figure 14C:
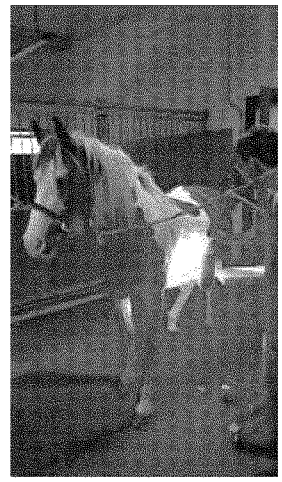
Figure 14D:
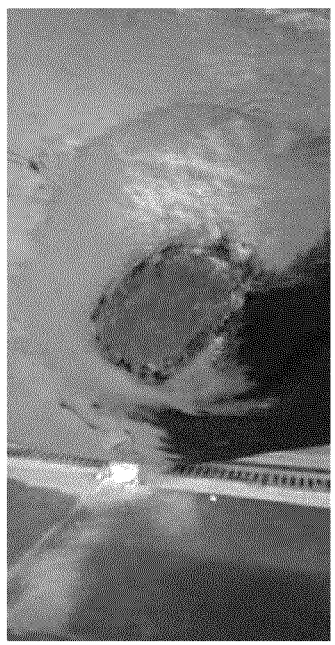
Figure 14D:
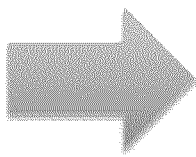
Figure 14D:
Figure 14E:
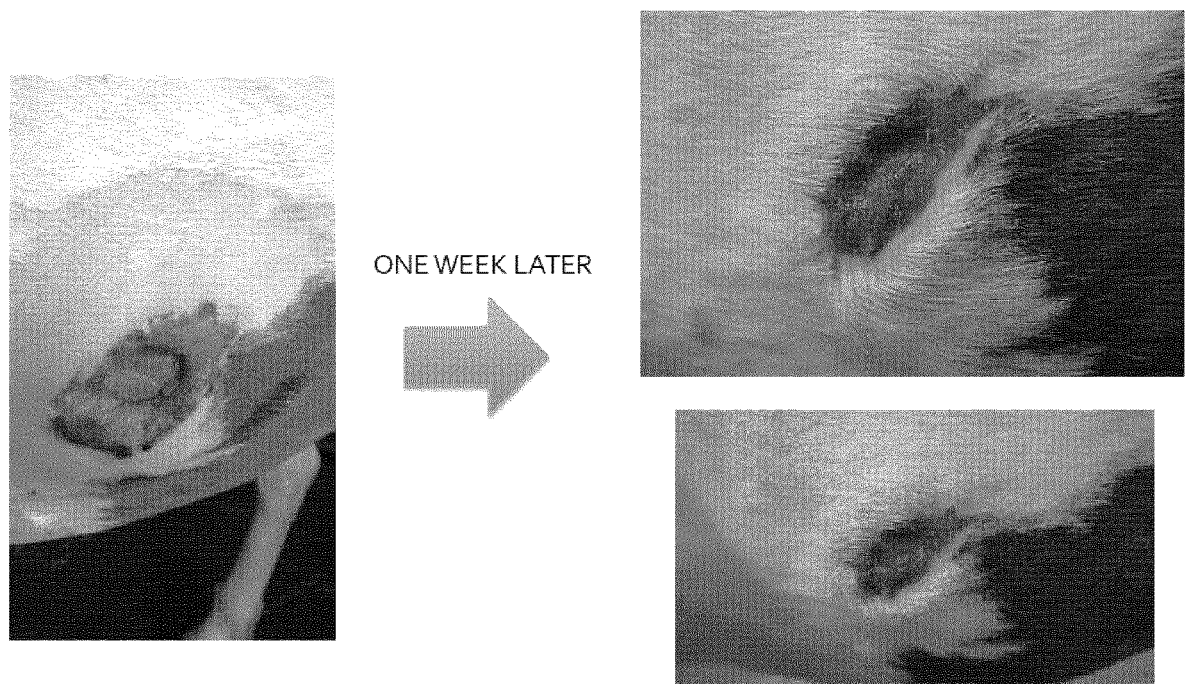

As shown in FIGS. 14A-14E, a 14 year old female, mixed breed horse with an old wound on the lateral surface of the chest was treated with biophotonic therapy. FIG. 14A shows treatment of the wound with lavage, disinfection, wound suture, drainage, and systemic antibiotic (conventional treatment). FIG. 14B shows dehiscence of the wound after conventional treatment. FIG. 14C shows treatment of the dehisced wound with a 12% UP biophotonic composition and blue light applied at a distance of 5 cm for five minutes. FIG. 14D shows healing of the wound after one week of treatment and before application of another round of biophotonic therapy. FIG. 14E shows healing of the wound after two applications of biophotonic therapy (two weeks of treatment). Healing time appeared to be reduced compared to that observed with conventional treatment. Additionally, antibiotic therapy was not required when biophotonic therapy was applied.

3. Use of Biophotonic Compositions for the Treatment of Periodontal Disease

The goal of this study was to evaluate the effects of biophotonic therapy on the treatment of moderate to advanced periodontal disease in dogs, such as in dogs with a periodontal disease at PD3 stage (moderate periodontitis with 25-50% attachment loss as measured either by the probing of the clinical attachment level, radiographic determination of the distance of the alveolar margin from cement-enamel junction relative to the length of the root, or a stage 2 furcation involvement in multi-rooted teeth) to PD4 stage (advanced periodontitis with >50% attachment loss as measured either by the probing of the clinical attachment level, or radiographic determination of the distance of the alveolar margin from the cement-enamel junction relative to the length of the root, or a stage 3 furcation involvement in multirooted teeth)

The impact of biophotonic therapy on the following parameters was assessed:
1. Impact on tissues (visual evaluation)
2. Ease of performing scaling and root planing
3. Probing pocket depth (PPD): mm
4. Bleeding on probing (BOP): +/−
5. Plaque index/Calculus index (PI/CI): 0-4
6. Plaque thickness/Calculus thickness (PT/CT): 1-3
7. Gingival index (GI): 0-3
8. Clinical attachment level (CAL): mm
9. Adverse events Twelve (12) dogs were evaluated. In each patient (dog), only the right half of the mouth was treated with a biophotonic composition followed by exposure of the treated area to blue light. The composition had 6% or 12% urea peroxide (UP), with six dogs treated with the 6% UP composition and 6 dogs treated with the 12% UP composition. The patients had to have a least two sites in each quadrant with a periodontal pocket (PP)≥4 mm or ≤10 mm. The PP is an extension of the normal gingival sulcus.

Figure 19A:
FIGS. 19A-19C present photographs of the first application of a biophotonic composition of the disclosure to a canine patient.
Figure 19A:
Figure 19B:
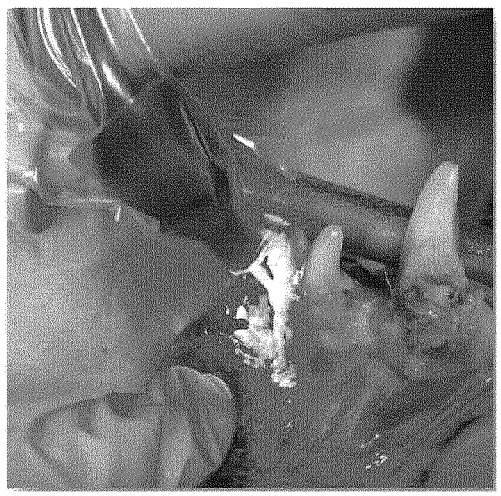
Figure 19B:
Figure 19C:
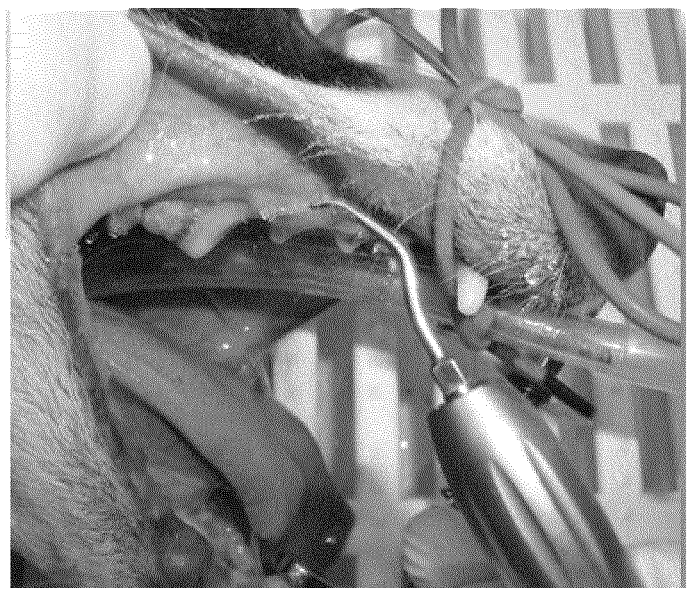
Figure 20A:
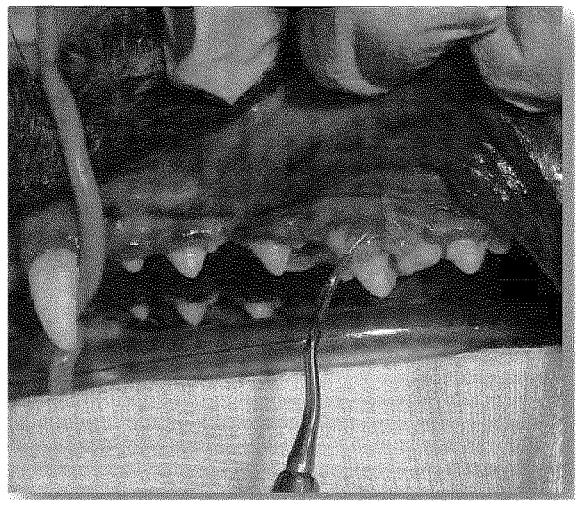
FIGS. 20A-20B present photographs of the second application of a biophotonic composition of the disclosure to a canine patient. The second application was applied once the SRP was completed.
Figure 20A:
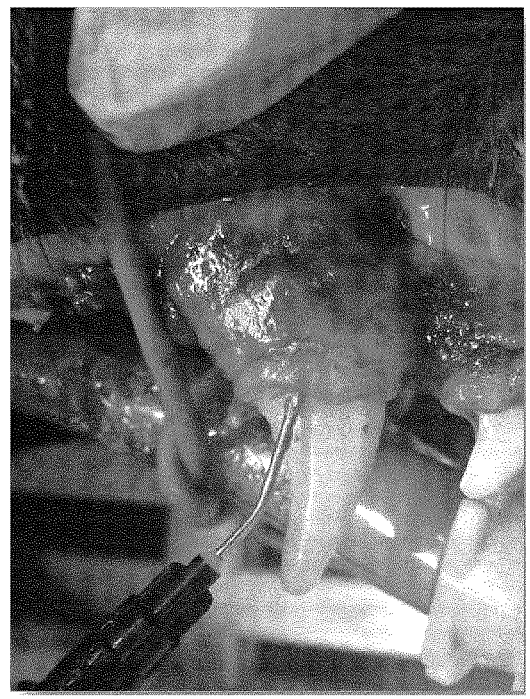
Figure 20B:
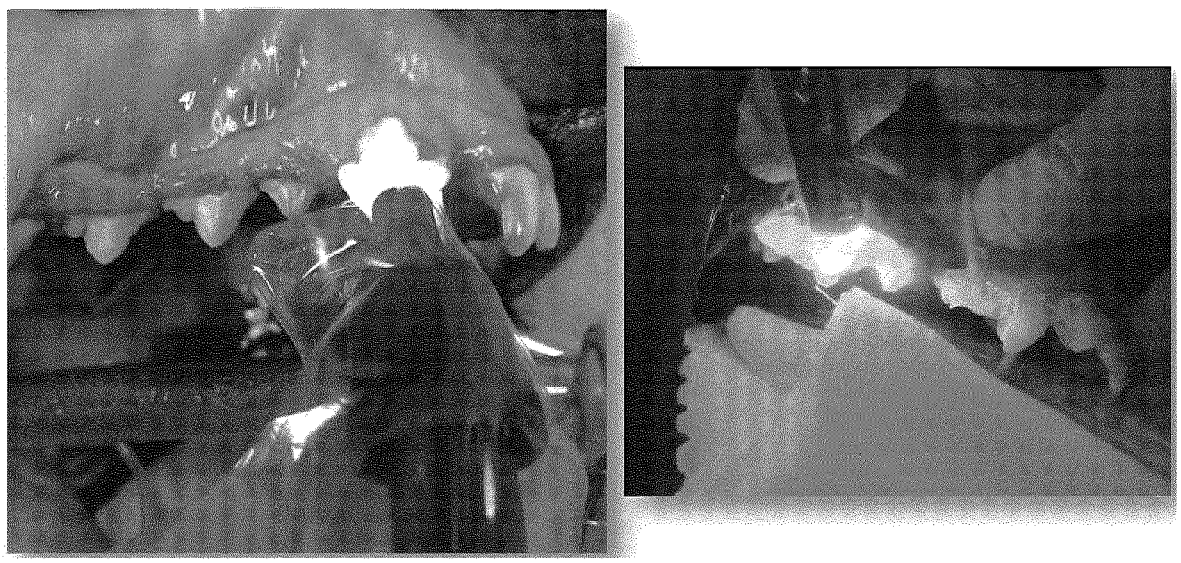

On the first treatment day (T0), a thin layer of the biophotonic composition of the disclosure (approximately 1 mm thick) was applied using a sterile dental syringe above the calculus and around the PP to be treated. The composition was then photoactivated by inserting into the PP the probe-like tip of the LED curing lamp (Bluephase® lamp (Ivoclar Vivadent AG, FL-9494 Schaan, Liechtenstein)) set at high power mode for two periods of 20 seconds (before and following scaling and root planing (SRP)). The first application was administered immediately prior to performing SRP (FIGS. 19A, 19B, and 19C), whereas the second application was applied once the SRP was completed (FIGS. 20A and 20B) and without any other co-procedures.

Figure 15:
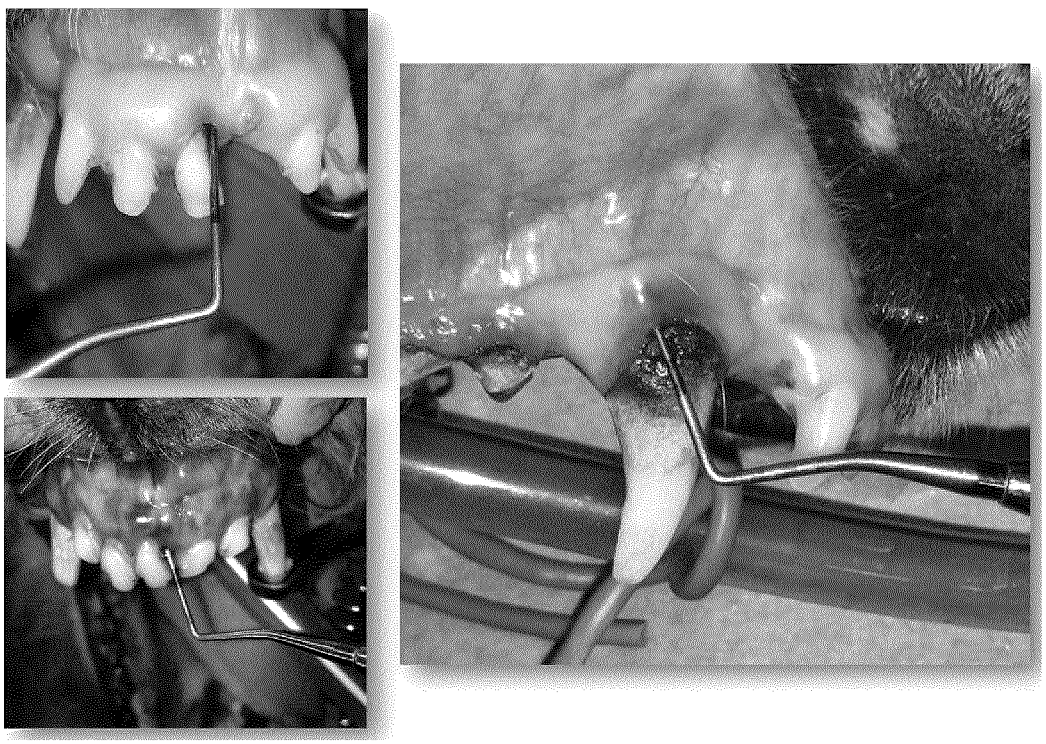
FIG. 15 presents photographs of measuring of probing pocket depth (PPD, in mm) of a canine patient.
Figure 16:
FIG. 16 presents a photograph of measuring of bleeding on probing (BOP) of a canine patient.
Figure 17:
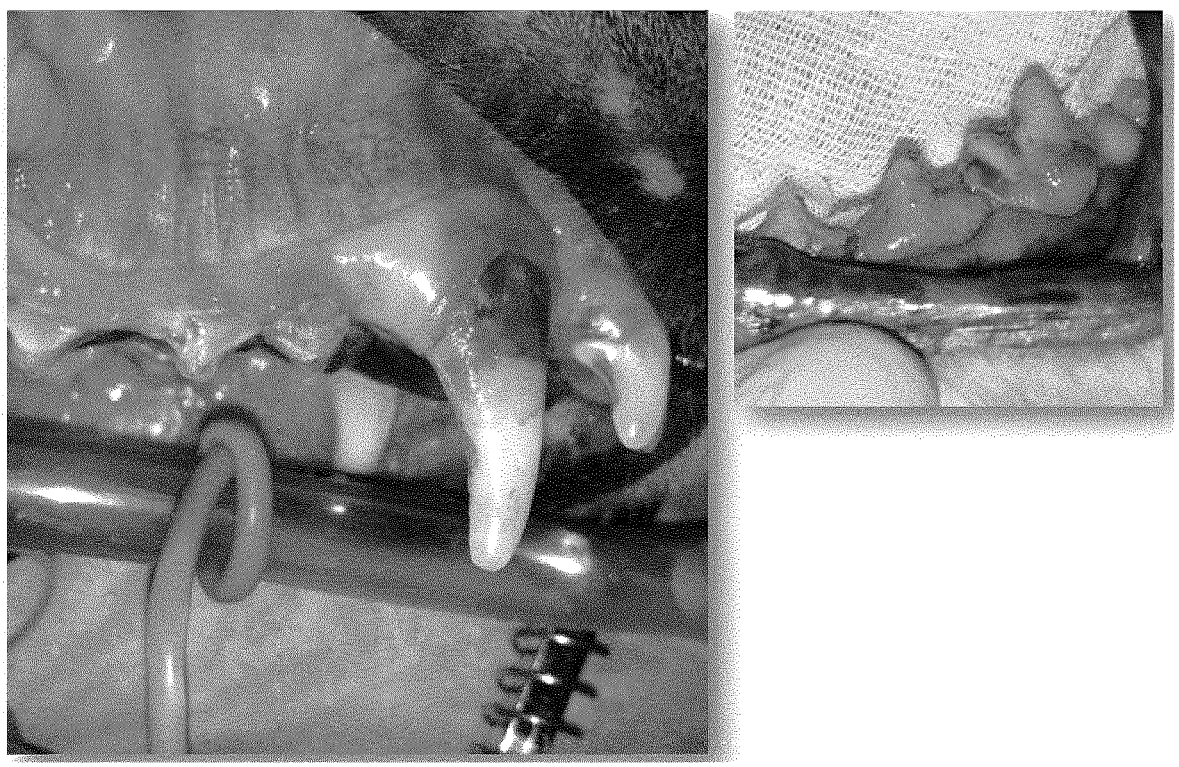
FIG. 17 present photographs of measuring of plaque index/calculus index (PT/CT) and plaque thickness/calculus thickness (PT/CT) of a canine patient.
Figure 18:
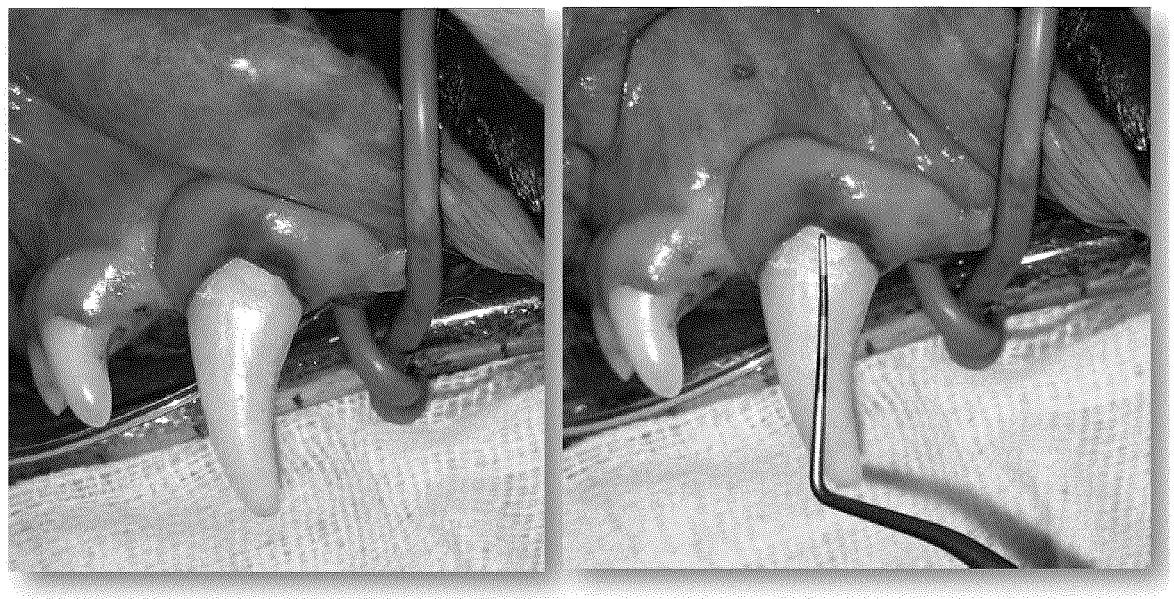
FIG. 18 present photographs of measuring of clinical attachment level (CAL, in mm) of a canine patient.
Figure 21:
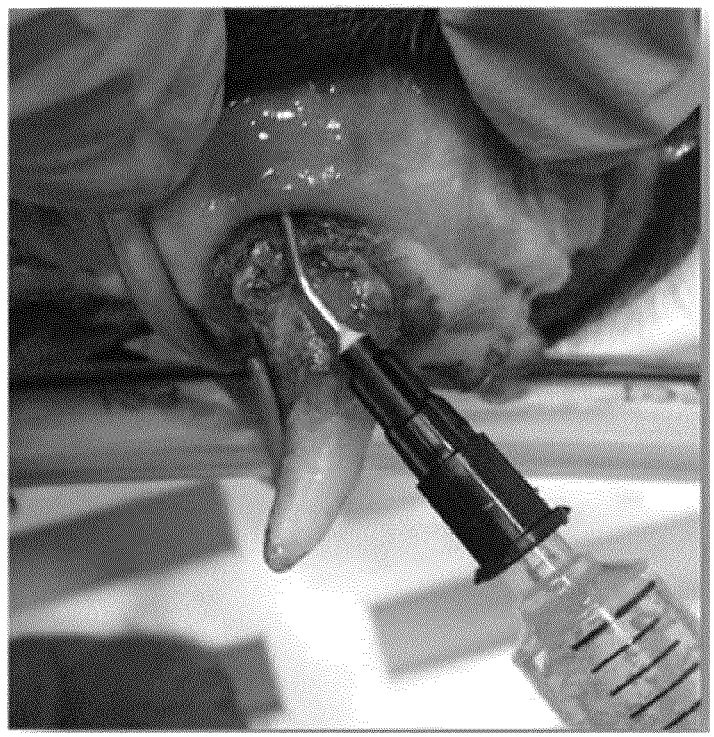
FIG. 21 presents a photograph of showing that the first application of biophotonic therapy considerably facilitated the performing of SRP and reduced the time required.

The following parameters were assessed at T0:
1. Impact on tissues (visual evaluation)
2. Ease of performing scaling and root planing
3. Probing pocket depth (PPD): mm (FIG. 15)
4. Bleeding on probing (BOP): +/− (FIG. 16)
5. Plaque index/Calculus index (PI/CI): 0-4 (FIG. 17)
6. Plaque thickness/Calculus thickness (PT/CT): 1-3 (FIG. 17)
7. Gingival index (GI): 0-3
8. Clinical attachment level (CAL): mm (FIG. 18)
9. Adverse events After 20 days (T1), the following parameters were assessed:
1. Probing pocket depth (PPD): mm
2. Bleeding on probing (BOP): +/−
3. Plaque index/Calculus index (PI/CI): 0-4
4. Plaque thickness/Calculus thickness (PT/CT): 1-3
5. Gingival index (GT): 0-3
6. Clinical attachment level (CAL): mm No adverse effects were found. The first application of biophotonic therapy considerably facilitated the performing of SRP and reduced the time required (FIG. 21).

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

The invention claimed is:

1. A method of treating a skin or soft tissue phlegmon wound having a resistant microbial infection that is resistant to treatment with an antimicrobial agent, the method comprising:
 a) applying a biophotonic composition to the skin or soft tissue phlegmon wound having a resistant microbial infection, wherein the biophotonic composition comprises at least one oxidant and at least one xanthene derivative dye for activating the oxidant; and
 b) exposing said biophotonic composition to actinic light having a peak wavelength from about 400 nm to about 700 nm for a period of less than about 5 minutes per $cm^2$ of an area to be treated; and wherein the at least one photoactivated xanthene derivative dye emits fluorescence light having a power density of between 0.005 $mW/cm^2$ to about 10 $mW/cm^2$;
 wherein said skin or soft tissue phlegmon wound is treated without antibiotics or antimicrobial agents.

2. The method according to claim 1, wherein the microbial infection is a bacterial infection.

3. The method according to claim 2, wherein the bacterial infection is resistant to antibiotics.

4. The method according to claim 1, wherein a source of said actinic light is positioned over an area to be treated, and wherein the source of actinic light is selected from the group consisting of a halogen lamp, a light-emitting diode lamp, a plasma arc lamp and a laser.

5. The method according to claim 1, wherein the oxidant is selected from the group consisting of hydrogen peroxide, carbamide peroxide, benzoyl peroxide, and mixtures thereof.

6. The method according to claim 1, wherein the composition further comprises a healing factor selected from the group consisting of hyaluronic acid, glucosamine, allantoin, and mixtures thereof.

7. The method according to claim 1, wherein the composition further comprises a gelling agent selected from the group consisting of glucose, modified starch, methyl cellulose, carboxymethyl cellulose, propyl cellulose, hydroxypropyl cellulose, a carbomer, alginic acid, sodium alginate, potassium alginate, ammonium alginate, calcium alginate, agar, carrageenan, locust bean gum, pectin, gelatin, and mixtures thereof.

8. The method according to claim 1, wherein the at least one xanthene derivative dye is a fluorone dye.

9. The method according to claim 8, wherein said fluorone dye is chosen from fluorescein and fluorescein derivatives.

10. The method according to claim 9, wherein said fluorescein derivative is selected from the group consisting of phloxine B, rose bengal, and merbromin.

11. The method according to claim 9, wherein said fluorescein derivative is selected from the group consisting of eosin Y, eosin B and erythrosine B.

12. The method according to claim 11, wherein said fluorescein derivative is eosin Y.

13. A method of maintaining asepsis during surgery of a skin or soft tissue phlegmon wound having a resistant microbial infection that is resistant to treatment with an antimicrobial agent, the method comprising:
 a) applying a biophotonic composition to the skin or soft tissue phlegmon wound having a resistant microbial infection, wherein the biophotonic composition comprises at least one oxidant and at least one xanthene derivative dye for activating the oxidant; and
 b) exposing said biophotonic composition to actinic light having a peak wavelength from about 400 nm to about 700 nm for a period of less than about 5 minutes per $cm^2$ of an area to be treated; and wherein the at least one photoactivated xanthene derivative dye emits fluorescence light having a power density of between 0.005 $mW/cm^2$ to about 10 $mW/cm^2$;
 wherein asepsis is maintained without antibiotics or antimicrobial agents.

* * * * *